(12) United States Patent
McDermott et al.

(10) Patent No.: US 11,478,581 B2
(45) Date of Patent: Oct. 25, 2022

(54) FLUID INJECTOR SYSTEM VOLUME COMPENSATION SYSTEM AND METHOD

(71) Applicant: BAYER HEALTHCARE LLC, Whippany, NJ (US)

(72) Inventors: Michael McDermott, Pittsburgh, PA (US); Michael Spohn, Fenelton, PA (US); William Barone, Pittsburgh, PA (US); Chelsea Marsh, Pittsburgh, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 371 days.

(21) Appl. No.: 16/621,164

(22) PCT Filed: Aug. 28, 2018

(86) PCT No.: PCT/US2018/048294
§ 371 (c)(1),
(2) Date: Dec. 10, 2019

(87) PCT Pub. No.: WO2019/046267
PCT Pub. Date: Mar. 7, 2019

(65) Prior Publication Data
US 2020/0093980 A1    Mar. 26, 2020

Related U.S. Application Data

(60) Provisional application No. 62/552,430, filed on Aug. 31, 2017.

(51) Int. Cl.
*A61M 5/00* (2006.01)
*A61M 5/14* (2006.01)
(Continued)

(52) U.S. Cl.
CPC .......... *A61M 5/007* (2013.01); *A61M 5/1408* (2013.01); *A61M 5/148* (2013.01);
(Continued)

(58) Field of Classification Search
CPC .......... A61M 5/14586; A61M 5/16881; A61M 2005/14208; A61M 2005/14553;
(Continued)

(56) References Cited

U.S. PATENT DOCUMENTS 383,858 A    6/1888   Campbell et al.
508,584 A    11/1893  Stevens
(Continued)

FOREIGN PATENT DOCUMENTS

CA    2045070 A1    2/1992
CA    2077712 A1    12/1993
(Continued)

OTHER PUBLICATIONS

SWISS; Medical Care., "CT Expres Contrast Media Delivery System Operation Manual Rev 1", 2004.
(Continued)

*Primary Examiner* — Jason E Flick
(74) *Attorney, Agent, or Firm* — David Schramm; Joseph L. Kent; James R. Stevenson

(57) ABSTRACT

A system and method for correcting a volume of fluid delivered by a fluid injector during an injection procedure is described. The method included determining and compensating for a volume factor associated with compliance of the fluid injector system and correcting for the volume by one of over-driving the distance that the drive member travels in a fluid reservoir, under-driving the distance that the drive member travels in the fluid reservoir, or lengthening or shortening a fluid delivery time.

20 Claims, 14 Drawing Sheets

(51) Int. Cl.
*A61M 5/142* (2006.01)
*A61M 5/145* (2006.01)
*A61M 5/148* (2006.01)
*A61M 5/168* (2006.01)

(52) U.S. Cl.
CPC .... *A61M 5/14228* (2013.01); *A61M 5/14546* (2013.01); *A61M 5/14586* (2013.01); *A61M 5/16877* (2013.01); *A61M 5/16881* (2013.01); *A61M 2005/14208* (2013.01); *A61M 2005/14553* (2013.01); *A61M 2205/3331* (2013.01); *A61M 2205/3389* (2013.01)

(58) Field of Classification Search
CPC .. A61M 2205/3331; A61M 2205/3362; A61M 2205/3389; A61M 2205/50; A61M 2205/702; A61M 5/007; A61M 5/1408; A61M 5/14228; A61M 5/1452; A61M 5/14546; A61M 5/148; A61M 5/168; A61M 5/1684; A61M 5/16854; A61M 5/16877; A61M 5/172; A61M 5/145; A61M 5/142; A61M 5/14; A61M 5/1407; A61M 5/14212; A61M 5/16831
See application file for complete search history.

(56) References Cited

U.S. PATENT DOCUMENTS

| | | |
|---|---|---|
| 945,143 A | 1/1910 | Iacques |
| 2,511,291 A | 6/1950 | Mueller |
| 2,583,206 A | 1/1952 | Borck et al. |
| 3,156,236 A | 11/1964 | Williamson |
| 3,159,312 A | 12/1964 | Van Sciver, II |
| 3,276,472 A | 10/1966 | Jinkens et al. |
| 3,349,713 A | 10/1967 | Fassbender |
| 3,520,295 A | 7/1970 | Paul |
| 3,523,523 A | 8/1970 | Heinrich et al. |
| 3,623,474 A | 11/1971 | Heilman |
| 3,635,444 A | 1/1972 | Potter |
| 3,671,208 A | 6/1972 | Wayne |
| 3,701,345 A | 10/1972 | Heilman |
| 3,719,207 A | 3/1973 | Takeda |
| 3,755,655 A | 8/1973 | Senegal |
| 3,793,600 A | 2/1974 | Grosbard |
| 3,812,843 A | 5/1974 | Wootten et al. |
| 3,817,843 A | 6/1974 | Barrett |
| 3,839,708 A | 10/1974 | Lyons et al. |
| 3,868,967 A | 3/1975 | Harding |
| 3,888,239 A | 6/1975 | Rubinstein |
| 3,895,220 A | 7/1975 | Nelson et al. |
| 3,898,983 A | 8/1975 | Elam |
| 3,927,955 A | 12/1975 | Spinosa et al. |
| 3,941,126 A | 3/1976 | Dietrich et al. |
| 3,958,103 A | 5/1976 | Oka et al. |
| 3,968,195 A | 7/1976 | Bishop |
| 3,995,381 A | 12/1976 | Manfred et al. |
| 4,001,549 A | 1/1977 | Corwin |
| 4,006,736 A | 2/1977 | Kranys et al. |
| 4,038,981 A | 8/1977 | Lefevre et al. |
| 4,044,757 A | 8/1977 | McWhorter et al. |
| 4,090,502 A | 5/1978 | Tajika |
| 4,135,247 A | 1/1979 | Gordon et al. |
| 4,151,845 A | 5/1979 | Clemens |
| 4,187,057 A | 2/1980 | Xanthopoulos |
| 4,191,183 A | 3/1980 | Mendelson |
| 4,199,000 A | 4/1980 | Edstrom |
| 4,204,775 A | 5/1980 | Speer |
| 4,207,871 A | 6/1980 | Jenkins |
| 4,208,136 A | 6/1980 | King et al. |
| 4,223,675 A | 9/1980 | Williams |
| 4,262,824 A | 4/1981 | Hrynewycz |
| 4,263,916 A | 4/1981 | Brooks et al. |
| 4,280,494 A | 7/1981 | Cosgrove, Jr. et al. |
| 4,284,073 A | 8/1981 | Krause et al. |
| 4,315,247 A | 2/1982 | Germanton |
| 4,319,568 A | 3/1982 | Tregoning |
| 4,329,067 A | 5/1982 | Goudy, Jr. |
| 4,340,153 A | 7/1982 | Spivey |
| 4,341,153 A | 7/1982 | Bowser |
| 4,392,847 A | 7/1983 | Whitney et al. |
| 4,392,849 A | 7/1983 | Petre et al. |
| 4,396,385 A | 8/1983 | Kelly et al. |
| 4,402,310 A | 9/1983 | Kimura |
| 4,409,966 A | 10/1983 | Lambrecht et al. |
| 4,434,820 A | 3/1984 | Glass |
| 4,434,822 A | 3/1984 | Bellamy et al. |
| 4,441,823 A | 4/1984 | Power et al. |
| 4,444,198 A | 4/1984 | Petre |
| 4,447,230 A | 5/1984 | Gula et al. |
| 4,448,200 A | 5/1984 | Brooks et al. |
| 4,474,476 A | 10/1984 | Thomsen |
| 4,477,923 A | 10/1984 | Baumann et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,504,908 A | 3/1985 | Riederer et al. |
| 4,509,526 A | 4/1985 | Barnes et al. |
| 4,512,764 A | 4/1985 | Wunsch |
| 4,542,459 A | 9/1985 | Riederer |
| 4,544,949 A | 10/1985 | Kurihara |
| 4,551,133 A | 11/1985 | Zegers et al. |
| 4,552,130 A | 11/1985 | Kinoshita |
| 4,559,036 A | 12/1985 | Wunsch |
| 4,563,175 A | 1/1986 | Lafond |
| 4,578,802 A | 3/1986 | Itoh |
| 4,585,009 A | 4/1986 | Barker et al. |
| 4,585,941 A | 4/1986 | Bergner |
| 4,610,670 A | 9/1986 | Spencer |
| 4,610,790 A | 9/1986 | Reti et al. |
| 4,611,340 A | 9/1986 | Okazaki |
| 4,612,572 A | 9/1986 | Komatsu et al. |
| 4,625,494 A | 12/1986 | Iwatschenko et al. |
| 4,626,144 A | 12/1986 | Berner |
| 4,633,307 A | 12/1986 | Honda |
| 4,634,426 A | 1/1987 | Kamen |
| 4,636,144 A | 1/1987 | Abe et al. |
| 4,655,197 A | 4/1987 | Atkinson |
| 4,662,906 A | 5/1987 | Matkovich et al. |
| 4,672,651 A | 6/1987 | Horiba et al. |
| 4,676,776 A | 6/1987 | Howson |
| 4,682,170 A | 7/1987 | Kubota et al. |
| 4,689,670 A | 8/1987 | Okazaki |
| 4,710,166 A | 12/1987 | Thompson et al. |
| 4,723,261 A | 2/1988 | Janssen et al. |
| 4,750,643 A | 6/1988 | Wortrich |
| 4,754,786 A | 7/1988 | Roberts |
| 4,781,687 A | 11/1988 | Wall |
| 4,783,273 A | 11/1988 | Knutsson et al. |
| 4,789,014 A | 12/1988 | Digianfilippo et al. |
| 4,793,357 A | 12/1988 | Lindstrom |
| 4,795,429 A | 1/1989 | Feldstein |
| 4,798,590 A | 1/1989 | O'Leary et al. |
| 4,804,454 A | 2/1989 | Asakura et al. |
| 4,823,833 A | 4/1989 | Hogan et al. |
| 4,835,521 A | 5/1989 | Andrejasich et al. |
| 4,836,187 A | 6/1989 | Iwakoshi et al. |
| 4,838,856 A | 6/1989 | Mulreany et al. |
| 4,840,620 A | 6/1989 | Kobayashi et al. |
| 4,844,052 A | 7/1989 | Iwakoshi et al. |
| 4,853,521 A | 8/1989 | Claeys et al. |
| 4,854,301 A | 8/1989 | Nakajima |
| 4,854,324 A | 8/1989 | Hirschman et al. |
| 4,857,056 A | 8/1989 | Talonn |
| 4,874,359 A | 10/1989 | White et al. |
| 4,879,880 A | 11/1989 | Harrison |
| 4,880,014 A | 11/1989 | Zarowitz et al. |
| 4,887,208 A | 12/1989 | Schneider et al. |
| 4,887,554 A | 12/1989 | Whitford |
| 4,901,731 A | 2/1990 | Millar |
| 4,903,705 A | 2/1990 | Imamura et al. |
| 4,913,154 A | 4/1990 | Ermert et al. |
| 4,922,916 A | 5/1990 | Ermert et al. |
| 4,925,444 A | 5/1990 | Orkin et al. |

(56) References Cited

U.S. PATENT DOCUMENTS

| | | |
|---|---|---|
| 4,929,818 A | 5/1990 | Bradbury et al. |
| 4,935,005 A | 6/1990 | Haines |
| 4,936,832 A | 6/1990 | Vaillancourt |
| 4,943,279 A | 7/1990 | Samiotes et al. |
| 4,943,779 A | 7/1990 | Pedersen et al. |
| 4,943,987 A | 7/1990 | Asahina et al. |
| 4,946,256 A | 8/1990 | Woodruff |
| 4,946,439 A | 8/1990 | Eggers |
| 4,947,412 A | 8/1990 | Mattson |
| 4,950,245 A | 8/1990 | Brown et al. |
| 4,952,068 A | 8/1990 | Flint |
| 4,954,129 A | 9/1990 | Giuliani et al. |
| 4,965,726 A | 10/1990 | Heuscher et al. |
| 4,966,579 A | 10/1990 | Polaschegg |
| 4,976,687 A | 12/1990 | Martin |
| 4,978,335 A | 12/1990 | Arthur, III |
| 4,981,467 A | 1/1991 | Bobo, Jr. et al. |
| 4,995,064 A | 2/1991 | Wilson et al. |
| 5,002,055 A | 3/1991 | Merki et al. |
| 5,004,472 A | 4/1991 | Wallace et al. |
| 5,009,654 A | 4/1991 | Minshall et al. |
| 5,010,473 A | 4/1991 | Jacobs |
| 5,013,173 A | 5/1991 | Shiraishi |
| 5,018,173 A | 5/1991 | Komai et al. |
| 5,032,112 A | 7/1991 | Fairchild et al. |
| 5,034,987 A | 7/1991 | Fujimoto et al. |
| 5,040,537 A | 8/1991 | Katakura |
| 5,053,002 A | 10/1991 | Barlow |
| 5,054,044 A | 10/1991 | Audon et al. |
| 5,056,568 A | 10/1991 | Digianfilippo et al. |
| 5,059,171 A | 10/1991 | Bridge et al. |
| 5,059,173 A | 10/1991 | Sacco |
| 5,061,243 A | 10/1991 | Winchell et al. |
| 5,069,662 A | 12/1991 | Bodden |
| 5,078,683 A | 1/1992 | Sancoff et al. |
| 5,088,981 A | 2/1992 | Howson et al. |
| 5,100,380 A | 3/1992 | Epstein et al. |
| 5,104,374 A | 4/1992 | Bishko et al. |
| 5,104,387 A | 4/1992 | Pokorney et al. |
| 5,108,365 A | 4/1992 | Woods, Jr. |
| 5,111,492 A | 5/1992 | Klausz |
| 5,113,905 A | 5/1992 | Pruitt et al. |
| 5,123,056 A | 6/1992 | Wilson |
| 5,123,121 A | 6/1992 | Broersma |
| 5,125,018 A | 6/1992 | Asahina |
| 5,128,121 A | 7/1992 | Berg et al. |
| 5,133,336 A | 7/1992 | Savitt et al. |
| 5,135,000 A | 8/1992 | Akselrod et al. |
| 5,140,862 A | 8/1992 | Pappalardo |
| 5,150,292 A | 9/1992 | Hoffmann et al. |
| 5,166,961 A | 11/1992 | Brunnett et al. |
| 5,180,895 A | 1/1993 | Briggs et al. |
| 5,180,896 A | 1/1993 | Gibby et al. |
| 5,190,744 A | 3/1993 | Rocklage et al. |
| 5,191,878 A | 3/1993 | Iida et al. |
| 5,196,007 A | 3/1993 | Ellman et al. |
| 5,199,604 A | 4/1993 | Palmer et al. |
| 5,207,642 A | 5/1993 | Orkin et al. |
| 5,215,095 A | 6/1993 | Macvicar et al. |
| 5,228,070 A | 7/1993 | Mattson |
| 5,230,614 A | 7/1993 | Zanger et al. |
| 5,242,390 A | 9/1993 | Goldrath |
| 5,249,122 A | 9/1993 | Stritzke |
| 5,249,579 A | 10/1993 | Hobbs et al. |
| 5,262,946 A | 11/1993 | Heuscher |
| 5,267,174 A | 11/1993 | Kaufman et al. |
| 5,269,756 A | 12/1993 | Dryden |
| 5,273,537 A | 12/1993 | Haskvitz et al. |
| 5,274,218 A | 12/1993 | Urata et al. |
| 5,276,614 A | 1/1994 | Heuscher |
| 5,286,252 A | 2/1994 | Tuttle et al. |
| 5,287,273 A | 2/1994 | Kupfer et al. |
| 5,295,967 A | 3/1994 | Rondelet et al. |
| 5,300,031 A | 4/1994 | Neer et al. |
| 5,301,656 A | 4/1994 | Negoro et al. |
| 5,301,672 A | 4/1994 | Kalender |
| 5,304,126 A | 4/1994 | Epstein et al. |
| 5,310,997 A | 5/1994 | Roach et al. |
| 5,311,568 A | 5/1994 | McKee, Jr. et al. |
| 5,313,992 A | 5/1994 | Grabenkort |
| 5,317,506 A | 5/1994 | Coutre et al. |
| 5,328,463 A | 7/1994 | Barton et al. |
| 5,329,459 A | 7/1994 | Kaufman et al. |
| 5,334,141 A | 8/1994 | Carr et al. |
| 5,339,799 A | 8/1994 | Kami et al. |
| 5,349,625 A | 9/1994 | Born et al. |
| 5,349,635 A | 9/1994 | Scott |
| 5,352,979 A | 10/1994 | Conturo |
| 5,354,273 A | 10/1994 | Hagen |
| 5,361,761 A | 11/1994 | Van et al. |
| 5,362,948 A | 11/1994 | Morimoto |
| 5,368,562 A | 11/1994 | Blomquist et al. |
| 5,368,567 A | 11/1994 | Lee |
| 5,368,570 A | 11/1994 | Thompson et al. |
| 5,373,231 A | 12/1994 | Boll et al. |
| 5,376,070 A | 12/1994 | Purvis et al. |
| 5,378,231 A | 1/1995 | Johnson et al. |
| 5,382,232 A | 1/1995 | Hague et al. |
| 5,383,231 A | 1/1995 | Yamagishi |
| 5,383,858 A | 1/1995 | Reilly et al. |
| 5,385,540 A | 1/1995 | Abbott et al. |
| 5,388,139 A | 2/1995 | Beland |
| 5,392,849 A | 2/1995 | Matsunaga et al. |
| 5,400,792 A | 3/1995 | Hoebel et al. |
| 5,417,213 A | 5/1995 | Prince |
| 5,431,627 A | 7/1995 | Pastrone et al. |
| 5,433,704 A | 7/1995 | Ross et al. |
| 5,445,621 A | 8/1995 | Poli et al. |
| 5,450,847 A | 9/1995 | Kaempfe et al. |
| 5,453,639 A | 9/1995 | Cronin et al. |
| 5,456,255 A | 10/1995 | Abe et al. |
| 5,458,128 A | 10/1995 | Polanyi et al. |
| 5,459,769 A | 10/1995 | Brown |
| 5,460,609 A | 10/1995 | O'Donnell |
| 5,464,391 A | 11/1995 | Devale |
| 5,468,240 A | 11/1995 | Gentelia et al. |
| 5,469,769 A | 11/1995 | Sawada et al. |
| 5,469,849 A | 11/1995 | Sasaki et al. |
| 5,472,403 A | 12/1995 | Cornacchia et al. |
| 5,474,683 A | 12/1995 | Bryant et al. |
| 5,485,831 A | 1/1996 | Holdsworth et al. |
| 5,489,265 A | 2/1996 | Montalvo et al. |
| 5,494,036 A | 2/1996 | Uber, III et al. |
| 5,494,822 A | 2/1996 | Sadri |
| 5,496,273 A | 3/1996 | Pastrone et al. |
| 5,507,412 A | 4/1996 | Ebert et al. |
| 5,515,851 A | 5/1996 | Goldstein |
| 5,522,798 A | 6/1996 | Johnson et al. |
| 5,531,679 A | 7/1996 | Schulman et al. |
| 5,531,697 A | 7/1996 | Olsen et al. |
| 5,533,978 A | 7/1996 | Teirstein |
| 5,544,215 A | 8/1996 | Shroy, Jr. et al. |
| 5,547,470 A | 8/1996 | Johnson et al. |
| 5,552,130 A | 9/1996 | Kraus et al. |
| 5,553,619 A | 9/1996 | Prince |
| 5,560,317 A | 10/1996 | Bunyan et al. |
| 5,566,092 A | 10/1996 | Wang et al. |
| 5,569,181 A | 10/1996 | Heilman et al. |
| 5,569,208 A | 10/1996 | Woelpper et al. |
| 5,573,515 A | 11/1996 | Wilson et al. |
| 5,579,767 A | 12/1996 | Prince |
| 5,583,902 A | 12/1996 | Bae |
| 5,590,654 A | 1/1997 | Prince |
| 5,592,940 A | 1/1997 | Kampfe et al. |
| 5,601,086 A | 2/1997 | Pretlow, III et al. |
| 5,611,344 A | 3/1997 | Bernstein et al. |
| 5,616,124 A | 4/1997 | Hague et al. |
| 5,681,285 A | 10/1997 | Ford et al. |
| 5,687,208 A | 11/1997 | Bae et al. |
| 5,687,708 A | 11/1997 | Farnsworth et al. |
| 5,713,358 A | 2/1998 | Mistretta et al. |
| 5,724,976 A | 3/1998 | Mine et al. |
| 5,725,500 A | 3/1998 | Micheler |
| 5,739,508 A | 4/1998 | Uber, III |

(56) References Cited

U.S. PATENT DOCUMENTS

| | | |
|---|---|---|
| 5,743,266 A | 4/1998 | Levene et al. |
| 5,768,405 A | 6/1998 | Makram-Ebeid |
| 5,796,862 A | 8/1998 | Pawlicki et al. |
| 5,799,649 A | 9/1998 | Prince |
| 5,800,397 A | 9/1998 | Wilson et al. |
| 5,806,519 A | 9/1998 | Evans, III et al. |
| 5,808,203 A | 9/1998 | Nolan, Jr. et al. |
| 5,827,219 A | 10/1998 | Uber, III et al. |
| 5,827,504 A | 10/1998 | Yan et al. |
| 5,840,026 A | 11/1998 | Uber, III et al. |
| 5,843,037 A | 12/1998 | Uber, III |
| 5,846,517 A | 12/1998 | Unger |
| 5,865,744 A | 2/1999 | Lemelson |
| 5,873,861 A | 2/1999 | Hitchins et al. |
| 5,881,124 A | 3/1999 | Giger et al. |
| 5,882,343 A | 3/1999 | Wilson et al. |
| 5,902,054 A | 5/1999 | Coudray |
| 5,903,454 A | 5/1999 | Hoffberg et al. |
| 5,916,165 A | 6/1999 | Duchon et al. |
| 5,920,054 A | 7/1999 | Uber, III |
| 5,947,935 A | 9/1999 | Kazousky et al. |
| 5,987,347 A | 11/1999 | Khoury et al. |
| 5,988,587 A | 11/1999 | Duchon et al. |
| 6,046,225 A | 4/2000 | Maddock |
| 6,055,985 A | 5/2000 | Bae et al. |
| 6,056,902 A | 5/2000 | Hettinga |
| 6,063,052 A | 5/2000 | Uber, III et al. |
| 6,073,042 A | 6/2000 | Simonetti |
| 6,099,502 A | 8/2000 | Duchon et al. |
| 6,113,568 A | 9/2000 | Olaussen |
| 6,132,396 A | 10/2000 | Antanavich et al. |
| 6,149,627 A | 11/2000 | Uber, III |
| 6,186,146 B1 | 2/2001 | Glickman |
| 6,201,889 B1 | 3/2001 | Vannah |
| 6,221,045 B1 | 4/2001 | Duchon et al. |
| 6,236,706 B1 | 5/2001 | Hsieh |
| 6,248,093 B1 | 6/2001 | Moberg |
| 6,306,117 B1 | 10/2001 | Uber, III |
| 6,313,131 B1 | 11/2001 | Lawyer |
| 6,317,623 B1 | 11/2001 | Griffiths et al. |
| 6,322,535 B1 | 11/2001 | Hitchins et al. |
| 6,344,030 B1 | 2/2002 | Duchon et al. |
| 6,381,486 B1 | 4/2002 | Mistretta et al. |
| 6,387,098 B1 | 5/2002 | Cole et al. |
| 6,397,093 B1 | 5/2002 | Aldrich |
| 6,397,097 B1 | 5/2002 | Requardt |
| 6,402,697 B1 | 6/2002 | Calkins et al. |
| 6,423,719 B1 | 7/2002 | Lawyer |
| 6,442,418 B1 | 8/2002 | Evans, III et al. |
| 6,470,889 B1 | 10/2002 | Bae et al. |
| 6,471,674 B1 | 10/2002 | Emig et al. |
| 6,478,735 B1 | 11/2002 | Pope et al. |
| 6,503,226 B1 | 1/2003 | Martinell et al. |
| 6,520,930 B2 | 2/2003 | Critchlow et al. |
| 6,527,718 B1 | 3/2003 | Connor et al. |
| 6,554,819 B2 | 4/2003 | Reich |
| 6,556,695 B1 | 4/2003 | Packer et al. |
| 6,572,851 B2 | 6/2003 | Muramatsu et al. |
| 6,574,496 B1 | 6/2003 | Golman et al. |
| 6,575,930 B1 | 6/2003 | Trombley, III et al. |
| 6,597,938 B2 | 7/2003 | Liu |
| 6,626,862 B1 | 9/2003 | Duchon et al. |
| 6,635,030 B1 | 10/2003 | Bae et al. |
| 6,643,537 B1 | 11/2003 | Zatezalo et al. |
| 6,652,489 B2 | 11/2003 | Trocki et al. |
| 6,656,157 B1 | 12/2003 | Duchon et al. |
| 6,673,033 B1 | 1/2004 | Sciulli et al. |
| 6,685,733 B1 | 2/2004 | Dae et al. |
| 6,691,047 B1 | 2/2004 | Fredericks |
| 6,699,219 B2 | 3/2004 | Emig et al. |
| 6,731,971 B2 | 5/2004 | Evans et al. |
| 6,754,521 B2 | 6/2004 | Prince |
| 6,775,764 B1 | 8/2004 | Batcher |
| 6,776,764 B2 | 8/2004 | Pinsky |
| 6,866,653 B2 | 3/2005 | Bae |
| 6,876,720 B2 | 4/2005 | Tsuyuki |
| 6,879,853 B2 | 4/2005 | Meaney et al. |
| 6,983,590 B2 | 1/2006 | Roelle et al. |
| 7,094,216 B2 | 8/2006 | Trombley, III et al. |
| 7,267,666 B1 | 9/2007 | Duchon et al. |
| 7,267,667 B2 | 9/2007 | Houde et al. |
| 7,292,720 B2 | 11/2007 | Horger et al. |
| 7,351,221 B2 | 4/2008 | Trombley et al. |
| 7,553,294 B2 | 6/2009 | Lazzaro et al. |
| 7,553,295 B2 | 6/2009 | Susi |
| 7,563,249 B2 | 7/2009 | Schriver et al. |
| 7,666,169 B2 | 2/2010 | Cowan et al. |
| 7,688,057 B2 | 3/2010 | Foss et al. |
| 7,861,893 B2 | 1/2011 | Voegele et al. |
| 7,925,330 B2 | 4/2011 | Kalafut et al. |
| 8,007,487 B2 | 8/2011 | Patrick et al. |
| 8,147,464 B2 | 4/2012 | Spohn et al. |
| 8,162,903 B2 | 4/2012 | Reilly et al. |
| 8,295,914 B2 | 10/2012 | Kalafut et al. |
| 8,337,456 B2 | 12/2012 | Schriver et al. |
| 8,377,003 B2 | 2/2013 | Wagner |
| 8,403,909 B2 | 3/2013 | Spohn et al. |
| 8,439,863 B2 | 5/2013 | Fago et al. |
| 8,486,017 B2 | 7/2013 | Masuda et al. |
| 8,905,969 B2 | 12/2014 | Nystrom et al. |
| 8,945,051 B2 | 2/2015 | Schriver et al. |
| 9,101,708 B2 | 8/2015 | Small et al. |
| 9,173,995 B1 | 11/2015 | Tucker et al. |
| 9,199,033 B1 | 12/2015 | Cowan et al. |
| 9,238,099 B2 | 1/2016 | Kalafut et al. |
| 9,242,083 B2 | 1/2016 | Fago et al. |
| 9,259,527 B2 | 2/2016 | Spohn et al. |
| 9,314,749 B2 | 4/2016 | Yagi et al. |
| 9,333,293 B2 | 5/2016 | Williams, Jr. et al. |
| 9,474,857 B2 | 10/2016 | Riley et al. |
| 9,555,379 B2 | 1/2017 | Schriver et al. |
| 9,901,671 B2 | 2/2018 | Toews et al. |
| 9,987,413 B2 | 6/2018 | Seibold et al. |
| 10,041,483 B2 | 8/2018 | Chappel et al. |
| 10,112,008 B2 | 10/2018 | Neftel et al. |
| 10,201,666 B2 | 2/2019 | Cowan et al. |
| 10,391,234 B2 | 8/2019 | Sams et al. |
| 10,549,084 B2 | 2/2020 | Sokolov et al. |
| 2001/0018937 A1 | 9/2001 | Nemoto |
| 2001/0027265 A1 | 10/2001 | Prince |
| 2001/0056233 A1 | 12/2001 | Uber et al. |
| 2002/0007116 A1 | 1/2002 | Zatezalo et al. |
| 2002/0010551 A1 | 1/2002 | Wang et al. |
| 2002/0026148 A1 | 2/2002 | Uber et al. |
| 2002/0099254 A1 | 7/2002 | Movahed |
| 2002/0123702 A1 | 9/2002 | Cho |
| 2002/0151854 A1 | 10/2002 | Duchon et al. |
| 2003/0050556 A1 | 3/2003 | Uber et al. |
| 2003/0120171 A1 | 6/2003 | Diamantopoulos et al. |
| 2003/0195462 A1 | 10/2003 | Mann et al. |
| 2003/0212364 A1 | 11/2003 | Mann et al. |
| 2003/0216683 A1 | 11/2003 | Shekalim |
| 2003/0226539 A1 | 12/2003 | Kim et al. |
| 2004/0011740 A1 | 1/2004 | Bernard et al. |
| 2004/0025452 A1 | 2/2004 | McLean |
| 2004/0044302 A1 | 3/2004 | Bernard et al. |
| 2004/0064041 A1 | 4/2004 | Lazzaro et al. |
| 2004/0092905 A1 | 5/2004 | Azzolini |
| 2004/0097806 A1 | 5/2004 | Hunter et al. |
| 2004/0154788 A1 | 8/2004 | Symonds |
| 2004/0162484 A1 | 8/2004 | Nemoto |
| 2004/0163655 A1 | 8/2004 | Gelfand et al. |
| 2004/0167415 A1 | 8/2004 | Gelfand et al. |
| 2004/0215144 A1 | 10/2004 | Duchon et al. |
| 2004/0253183 A1 | 12/2004 | Uber, III et al. |
| 2004/0254533 A1 | 12/2004 | Schriver et al. |
| 2005/0107697 A1 | 5/2005 | Berke et al. |
| 2005/0171487 A1 | 8/2005 | Haury et al. |
| 2005/0234407 A1 | 10/2005 | Spohn et al. |
| 2005/0234428 A1 | 10/2005 | Spohn et al. |
| 2006/0052794 A1 | 3/2006 | McGill et al. |
| 2006/0079765 A1 | 4/2006 | Neer et al. |
| 2006/0079843 A1 | 4/2006 | Brooks et al. |
| 2006/0167415 A1 | 7/2006 | Nemoto |

(56) References Cited

U.S. PATENT DOCUMENTS

| | | | |
|---|---|---|---|
| 2007/0068964 A1 | 3/2007 | Tanaami et al. |
| 2007/0129705 A1 | 6/2007 | Trombley, III et al. |
| 2007/0161970 A1 | 7/2007 | Spohn et al. |
| 2007/0219496 A1 | 9/2007 | Kamen et al. |
| 2007/0276327 A1 | 11/2007 | Kalafut et al. |
| 2008/0045925 A1 | 2/2008 | Stepovich et al. |
| 2008/0086087 A1 | 4/2008 | Spohn et al. |
| 2008/0167621 A1 | 7/2008 | Wagner et al. |
| 2008/0183131 A1 | 7/2008 | Duchon et al. |
| 2009/0112164 A1 | 4/2009 | Reilly et al. |
| 2009/0216192 A1 | 8/2009 | Schriver et al. |
| 2009/0234226 A1 | 9/2009 | Nemoto |
| 2009/0247865 A1 | 10/2009 | Spohn et al. |
| 2009/0247961 A1 | 10/2009 | Carlyon |
| 2009/0312744 A1 | 12/2009 | Keeley et al. |
| 2010/0130809 A1 | 5/2010 | Morello |
| 2010/0222768 A1* | 9/2010 | Spohn ................ A61M 5/1452 604/506 |
| 2010/0249586 A1 | 9/2010 | Cocker et al. |
| 2010/0262078 A1 | 10/2010 | Blomquist |
| 2010/0331779 A1 | 12/2010 | Nystrom et al. |
| 2011/0275988 A1 | 11/2011 | Davis et al. |
| 2012/0089114 A1 | 4/2012 | Hemond et al. |
| 2012/0101472 A1 | 4/2012 | Schroeder et al. |
| 2012/0178629 A1 | 7/2012 | Hudson et al. |
| 2012/0203177 A1 | 8/2012 | Lanier, Jr. et al. |
| 2012/0204997 A1 | 8/2012 | Winn et al. |
| 2012/0217231 A1 | 8/2012 | Moore et al. |
| 2012/0245560 A1 | 9/2012 | Hochman |
| 2013/0245439 A1 | 9/2013 | Small et al. |
| 2013/0245604 A1 | 9/2013 | Kouyoumjian et al. |
| 2013/0261993 A1 | 10/2013 | Ruchti et al. |
| 2014/0027009 A1 | 1/2014 | Riley et al. |
| 2014/0276550 A1 | 9/2014 | Uram et al. |
| 2016/0030662 A1 | 2/2016 | Uber, III et al. |
| 2016/0278725 A1 | 9/2016 | Van Nijnatten |
| 2016/0331896 A1 | 11/2016 | Nemoto et al. |
| 2017/0035974 A1 | 2/2017 | Berry et al. |
| 2017/0143898 A1 | 5/2017 | Grosse-Wentrup et al. |
| 2017/0258982 A1 | 9/2017 | Kemper |
| 2017/0290971 A1 | 10/2017 | Hedmann et al. |
| 2017/0343446 A1 | 11/2017 | Ciolkosz et al. |
| 2018/0133392 A1 | 5/2018 | Dembo et al. |
| 2019/0083699 A1 | 3/2019 | Spohn et al. |

FOREIGN PATENT DOCUMENTS

| | | |
|---|---|---|
| CA | 2234050 A1 | 4/1997 |
| CN | 1671428 A | 9/2005 |
| CN | 103347552 A | 10/2013 |
| DE | 3203594 A1 | 8/1983 |
| DE | 3726452 A1 | 2/1989 |
| DE | 4426387 A1 | 8/1995 |
| DE | 19702896 A1 | 7/1997 |
| DE | 19647701 A1 | 5/1998 |
| DE | 19919572 A1 | 11/2000 |
| EP | 0121216 A1 | 10/1984 |
| EP | 0129910 A1 | 1/1985 |
| EP | 0189491 A1 | 8/1986 |
| EP | 0192786 A2 | 9/1986 |
| EP | 0245160 A1 | 11/1987 |
| EP | 0319275 A1 | 6/1989 |
| EP | 0337924 A2 | 10/1989 |
| EP | 0343501 A2 | 11/1989 |
| EP | 0364966 A1 | 4/1990 |
| EP | 0365301 A1 | 4/1990 |
| EP | 0372152 A1 | 6/1990 |
| EP | 0378896 A2 | 7/1990 |
| EP | 0429191 A2 | 5/1991 |
| EP | 0471455 A2 | 2/1992 |
| EP | 0475563 A1 | 3/1992 |
| EP | 0595474 A2 | 5/1994 |
| EP | 0600448 A1 | 6/1994 |
| EP | 0619122 A1 | 10/1994 |
| EP | 0439711 B1 | 5/1995 |
| EP | 0869738 A1 | 10/1998 |
| EP | 1016427 A2 | 7/2000 |
| EP | 2990073 A1 | 3/2016 |
| FR | 2493708 A1 | 5/1982 |
| FR | 2561949 A1 | 10/1985 |
| GB | 201800 A | 8/1923 |
| GB | 2252656 A | 8/1992 |
| GB | 2328745 A | 3/1999 |
| JP | S5017781 A | 2/1975 |
| JP | S5815842 A | 1/1983 |
| JP | S59214432 A | 12/1984 |
| JP | S60194934 A | 10/1985 |
| JP | S60194935 A | 10/1985 |
| JP | S60253197 A | 12/1985 |
| JP | S62216199 A | 9/1987 |
| JP | S6340538 A | 2/1988 |
| JP | S63290547 A | 11/1988 |
| JP | H01207038 A | 8/1989 |
| JP | H02224647 A | 9/1990 |
| JP | H02234747 A | 9/1990 |
| JP | H0355040 A | 3/1991 |
| JP | H04115677 A | 4/1992 |
| JP | H0584296 A | 4/1993 |
| JP | H07178169 A | 7/1995 |
| JP | H0849598 A | 2/1996 |
| JP | H0999034 A | 4/1997 |
| JP | H10211198 A | 8/1998 |
| JP | 2000175900 A | 6/2000 |
| JP | 2003102724 A | 4/2003 |
| JP | 2003116843 A | 4/2003 |
| JP | 2003210456 A | 7/2003 |
| JP | 2003225234 A | 8/2003 |
| JP | 2004174008 A | 6/2004 |
| JP | 2004236849 A | 8/2004 |
| JP | 2004298550 A | 10/2004 |
| JP | 4960180 B2 | 6/2012 |
| JP | 5063593 B2 | 10/2012 |
| JP | 5203971 B2 | 6/2013 |
| JP | 5227791 B2 | 7/2013 |
| JP | 5490840 B2 | 5/2014 |
| WO | 8001754 A1 | 9/1980 |
| WO | 8500292 A1 | 1/1985 |
| WO | 8803815 A1 | 6/1988 |
| WO | 9114232 A1 | 9/1991 |
| WO | 9114233 A1 | 9/1991 |
| WO | 9315658 A1 | 8/1993 |
| WO | 9325141 A1 | 12/1993 |
| WO | 9415664 A1 | 7/1994 |
| WO | 9632975 A1 | 10/1996 |
| WO | 9712550 A1 | 4/1997 |
| WO | 9820919 A1 | 5/1998 |
| WO | 9924095 A2 | 5/1999 |
| WO | 0061216 A1 | 10/2000 |
| WO | 0141835 A2 | 6/2001 |
| WO | 03015633 A1 | 2/2003 |
| WO | 2004012787 A2 | 2/2004 |
| WO | 2004035116 A1 | 4/2004 |
| WO | 2004091688 A2 | 10/2004 |
| WO | 2005016165 A1 | 2/2005 |
| WO | 2005035995 A1 | 4/2005 |
| WO | 2006042093 A1 | 4/2006 |
| WO | 2007079016 A2 | 7/2007 |
| WO | 2007092618 A2 | 8/2007 |
| WO | 2007116862 A1 | 10/2007 |
| WO | 2007116891 A1 | 10/2007 |
| WO | 2007133942 A1 | 11/2007 |
| WO | 2008078604 A1 | 7/2008 |
| WO | 2008106108 A1 | 9/2008 |
| WO | 2009051995 A1 | 4/2009 |
| WO | 2010027636 A1 | 3/2010 |
| WO | 2010117841 A1 | 10/2010 |
| WO | 2011125303 A1 | 10/2011 |
| WO | 2012048277 A2 | 4/2012 |
| WO | 2012155035 A1 | 11/2012 |
| WO | 2013043868 A1 | 3/2013 |
| WO | 2014144651 A2 | 9/2014 |
| WO | 2014179326 A1 | 11/2014 |
| WO | 2014190264 A1 | 11/2014 |

(56) References Cited

FOREIGN PATENT DOCUMENTS

| WO | 2015106107 A1 | 7/2015 |
|---|---|---|
| WO | 2015164783 A1 | 10/2015 |
| WO | 2016112163 A1 | 7/2016 |
| WO | 2016172467 A1 | 10/2016 |
| WO | 2016191485 A1 | 12/2016 |
| WO | 2017038575 A1 | 3/2017 |
| WO | 2017096072 A1 | 6/2017 |
| WO | 2017152036 A1 | 9/2017 |
| WO | 2018060505 A1 | 4/2018 |
| WO | 2018075386 A1 | 4/2018 |
| WO | 2018089882 A1 | 5/2018 |

OTHER PUBLICATIONS

Ostergaard, L., et al., "High resolution measurement of cerebral blood flow using intravascular tracer boluspassages. Part 1: Mathematical approach and statistical analysis," Magnetic Resonance in Medicine, vol. 36, Issue 5,pp. 715-725 (Nov. 1996).

Ostergaard, L., et al., "High resolution measurement of cerebral blood flow using intravascular tracer boluspassages. Part II: Experimental comparison and preliminary results," Magn Reson Med, vol. 36, Issue 5, pp. 726-736(Nov. 1996).

Parker, K.J., et al., "A Particulate Contrast Agent With Potential for Ultrasound Imaging of Liver," Ultrasound in Medicine & Biology, vol. 13, Issue 9, pp. 555-566 (Sep. 1987).

Rosen, B.R. et al., "Perfusion Imaging with NMR Contrast Agents," Magentic Resonance in Medicine, vol. 14, No. 2, pp. 249-265, May 1, 1990.

Sablayrolles, J-L, "Cardiac CT: Experience from Daily Practice", Advance CT, A GE Healthcare Publication. Aug. 2004.

Stevens, M.A., et al. "A Prospective Randomized Trial of Prevention Measures in Patients at High Risk for Contrast Nephropathy," J. of the ACC, vol. 33, Issue 2, pp. 403-411, Feb. 1999.

Wada D.R. and Ward; D.S., "The hybrid model: a new pharmacokinetic model for computer-controlled infusion pumps", IEEE Transactions on Biomedical Engineering, 1994, vol. 41, Issue 2, pp. 134-142.

Wada, D.R. and Ward, D.S., "Open loop control of multiple drug effects in anesthesia", IEEE Transactions on Biomedical Engineering, vol. 42, Issue 7, pp. 666-677, 1995.

Yamashita, Y. et al., "Abdominal Helical CT: Evaluation of Optimal Doses of Intravenous Contrast Material—A Prospective Randomized Study," Radiology, vol. 216, Issue 3, pp. 718-723, Sep. 1, 2000. Angiography, Catheterization and Cardiovascular Diagnosis, vol. 19, pp. 123-128, 1990.

Awai Kazuo; et al., "Aortic and Hepatic Enhancement and Tumor-to-Liver Contrast: Analysis of the Effect of Different Concentrations of Contrast Material at Multi-Detector Row Helical CT.", Radiology, 2002, vol. 224; Issue 3., 757-763.

Angelini, P.," Use of mechanical injectors during percutaneous transluminal coronary angioplasty (PTCA)," Catheterization and Cardiovascular Diagnosis, vol. 16, Issue 3, pp. 193-194, Mar. 1989.

Awai, K., et al., "Effect of contrast material injection duration and rate on aortic peak time and peak enhancement at dynamic CT involving injection protocol with dose tailored to patient weight," Radiology, vol. 230, Issue 1, pp. 142-150, 2004.

Bae, et al. "Aortic and Hepatic Contrast Medium Enhancement at CT—Part I, Prediction with a Computer Model", Radiology 1998;207:647-655.

Bae, K.T., et al., "Multiphasic Injection Method for Uniform Prolonged Vascular Enhancement at CT Angiography: Pharmacokinetic Analysis and Experimental Porcine Model," Radiology, vol. 216, Issue 3, pp. 872-880 (Sep. 2000).

Bae, K.T. et al, "Peak Contrast Enhancement in CT and MR Angiography: When Does it Occur and Why? Pharmacokinetic Study in a Porcine Model", Radiology, vol. 227, Jun. 2003, pp. 809-816.

Bae, K.T., et al., "Uniform vascular contrast enhancement and reduced contrast medium volume achieved by using exponentially decelerated contrast material injection method," Radiology, vol. 231, Issue 3, pp. 732-736, 2004.

Baker, Aaron; et al. "Fluid Mechanics Analysis of a Spring-Loaded Jet Injector." IEEE Transactions on Biomedical Engineering, vol. 46, No. 2, Feb. 1999.

Becker, C.R., et al., "Optimal contrast application for cardiac 4-detector-row computed tomography," Investigative Radiology, vol. 38, Issue 11, pp. 690-694 (Nov. 2003).

Blomley, M.J.K. and Dawson, P., "Bolus Dynamics: Theoretical and Experimental Aspects," The Brit. J. ofRadiology, vol. 70, No. 832, pp. 351-359 (Apr. 1997).

Brunette J.; et al., "Comparative rheology of low- and iso-osmolarity contrast agents at different temperature", Catheterization and Cardiovascular Interventions, 2008, vol. 71 Issue No. 1, 78-83.

Cademartiri, F. and Luccichenti, G., et al. "Sixteen-row multislice computed tomography: basic concepts, protocols, and enhanced clinical applications," Seminars in Ultrasound, CT and MRI, vol. 25, Issue 1, pp. 2-16, 2004.

Dardik, H. et al., "Remote Hydraulic Syringe Actuator," Arch. Surg., vol. 115, Issue 1, Jan. 1980.

Dawson, P. and Blomley, M., "The value of mathematical modelling in understanding contrast enhancement in CT with particular reference to the detection of hypovascular liver metastases," European Journal of Radiology, vol. 41, Issue 3, pp. 222-36 (Mar. 2002).

"Digital Injector for Angiography", Sias. (Sep. 7, 1993).

Disposable Low-Cost Catheter Tip Sensor Measures Blood Pressure during Surgery, Sensor (Jul. 1989).

EZ CHEM Brochure, E-Z-EM, Inc. (Jul. 2007).

Fisher, M.E. and Teo, K.L., "Optimal insulin infusion resulting from a mathematical model of blood glucose dynamics", IEEE Transactions on Biomedical Engineering, vol. 36, Issue 4, pp. 479-486, 1989.

Flegal, K.M., et al., "Prevalence and trends in obesity among US adults," JAMA, 2002, vol. 288, Issue 14, pp. 1-4, (1999-2000).

Fleischmann, D. and Hittmair, K., "Mathematical analysis of arterial enhancement and optimization of bolus geometry for CT angiography using the discrete Fourier transform," Journal of Computer Assisted Tomography, vol. 23, Issue 3, pp. 474-484 (May/Jun. 1999).

Fleischmann, D., "Contrast Medium Injection Technique," In: U. Joseph Schoepf: "Multidetector—Row CT of the Thorax," pp. 47-59 (Jan. 22, 2004).

Fleischmann, D., "Present and Future Trends in Multiple Detector—Row CT Applications; CT Angiography", European Radiology, vol. 12, Issue 2, Supplement 2, Jul. 2002, pp. s11-s15.

Gardiner, G. A., et al., "Selective Coronary Angiography Using a Power Injector," AJR Am J Roentgenol., vol. 146, Issue 4, pp. 831-833 (Apr. 1986).

Garrett, J. S., et al., "Measurement of cardiac output by cine computed tomography," The American Journal of Cardiology, vol. 56, Issue 10, pp. 657-661, 1985.

Gembicki, F.W., "Vector Optimization for Control with Performance and Parameter Sensitivity Indices," PhD Thesis Case Western Reserve University, 1974.

Gentilini A., et al., "A new paradigm for the closed-loop intraoperative administration of analgesics in humans," IEEE Transactions on Biomedical Engineering, vol. 49, Issue 4, pp. 289-299 (Apr. 2002).

Gerlowski L.E. and Jain R.K., "Physiologically Based Pharmacokinetic Modeling: Principles and Applications," Journal of Pharmaceutical Sciences, vol. 72, pp. 1104-1125, Oct. 1983.

Goss, J. E., et al., "Power injection of contrast media during percutaneous transluminal coronary artery angioplasty," Catheterization and Cardiovascular Diagnosis, vol. 16, Issue 3, pp. 195-198 (Mar. 1989).

Grant, S.C.D. et al., "Reduction of Radiation Exposure to the Cardiologist during Coronary Angiography by the Use of a Remotely Controlled Mechanical Pump for Injection of Contrast Medium," Catheterization and Cardiovascular Diagnosis, vol. 25, Issue 2, pp. 107-109 (Feb. 1992).

Hackstein, N. et al., "Glomerular Filtration Rate Measured by Using Triphasic Helical CT with a Two-Point Patlak Plot Technique," Radiology, vol. 230, Issue 1, pp. 221-226, Jan. 2004.

Hansen, P.C, Regularization tools: a MATLAB package for analysis and solution of discrete ill-posed problems, Numerical Algorithms, vol. 6, Issue 1, pp. 35, 1994.

(56) References Cited

OTHER PUBLICATIONS

Hansen, P.C., "The truncated SVD as a method for regularization," BIT Numerical Mathematics, vol. 27, Issue 4, pp. 534-555, 1987.
Harris P., H. D. "The Human Pulmonary Circulation," Edinburgh, Churchill Livingstone, (Appendix I), 1986.
Hayes, M., "Statistical Digital Signal Processing and Modeling", New York, New York, Wiley and Sons, 1996, pp. 154-177, (Prony's method).
Heiken; J.P. et al., "Dynamic Contrast-Enhanced CT of the Liver: Comparison of Contrast Medium Injection Rates and Uniphasic and Biphasic Injection Protocols", Radiology, May 1993, vol. 187, No. 2, pp. 327-331.
"Infus O.R. Multi-Drug Syringe Pump with Smart Labels," Bard MedSystems Division Inc., pp. 2693-2696 (2005).
"International Preliminary Report on Patentability from PCT Application No. PCT/US2018/048294", dated Mar. 12, 2020.
Ireland, M.A., et al., "Safety and Convenience of a Mechanical Injector Pump for Coronary Angiography,"Catheterization and Cardiovascular Diagnosis, vol. 16, Issue 3, pp. 199-201 (1989).
Jacobs, J.R., "Algorithm for optimal linear model-based control with application to pharmacokinetic model-driven drug delivery," IEEE Transactions on Biomedical Engineering, vol. 37, Issue 1, pp. 107-109 (Jan. 1990).
Korosec, F.R., "Physical Principles of Phase-Contrast, Time-of-Flight, and Contrast-Enhanced MR Angiography," 41st Annual Meeting of American Association of Physicists in Medicine, Jul. 25-29, 1999.
Korosec, Frank, "Basic Principles of Phase-contrast, Time-of-flight, and Contrast-enhanced MR Angiography", 1999.
Krause, W, "Application of pharmacokinetics to computed tomography: injection rates and schemes: mono-, bi-, or multiphasic?," Investigative Radiology, vol. 31, Issue 2, pp. 91-100, Feb. 1996.
Krieger, R. A., "CO2-Power-Assisted Hand-Held Syringe: Better Visualization during Diagnostic and InterventionalAngiography," Cathet Cardiovasc Diagn., vol. 19, Issue 2, pp. 123-128 (Feb. 1990).
Liebel-Flarsheim Company, "Angiomat 6000 Digital Injection System—Operator's Manual", Document No. 600950, Rev. 1, Jan. 1990.
Mahnken, A. H., et al., "Determination of cardiac output with multislice spiral computed tomography: a validation study," Investigative Radiology, vol. 39, Issue 8, pp. 451-454, Aug. 2004.
Mahnken, A. H., et al., "Measurement of cardiac output from a test-bolus injection in multislice computed tomography," European Radiology, vol. 13, Issue 11, pp. 2498-2504, 2003.
Mark V/Mark V Plus Injector Operation Manual KMP 805P Rev. B. MEDRAD, Inc, 1990.
McClellan, J.H., "Parametric Signal Modeling," Chapter 1 in Advanced Topics in Signal Processing, Pentice-Hall, Englewood Cliffs, NJ (1988).
MCT and MCT Plus Injection Systems Operation Manual KMP 810P, MEDRAD, Inc, 1991.
Morden Peter.; et al., "The Role of Saline Flush Injection Rate in Displacement of CT Injectable Peripherally Inserted Central Catheter Tip During Power Injection of Contrast Material", AJR, Jan. 2014, 202, W13-W18.
Neatpisarnvanit, C. and Boston, J.R., "Estimation of plasma insulin from plasma glucose", IEEE Transactions an Biomedical Engineering, vol. 49, Issue 11, pp. 1253-1259, 2002.

\* cited by examiner

FLUID INJECTOR SYSTEM VOLUME COMPENSATION SYSTEM AND METHOD

CROSS REFERENCE TO RELATED APPLICATIONS

This application is a § U.S. national phase application under 35 U.S.C. § 371 of PCT International Application No. PCT/US2018/048294, filed 28 Aug. 2018 and claims priority to U.S. Provisional Application No. 62/552,430, titled "Fluid Injector System Volume Compensation System and Method" and filed on 31 Aug. 2017, the disclosures of which are incorporated herein in their entirety

BACKGROUND

Field of the Disclosure

The present disclosure relates generally to a system and method for calibrating a fluid injector, such as a medical fluid injector, and, further, to a system and method for compensating for over-delivery or under-delivery of fluid during an injection procedure.

Description of Related Art

In many medical diagnostic and therapeutic procedures, a medical practitioner, such as a physician, injects a patient with one or more medical fluids. In recent years, a number of fluid delivery systems having injector-actuated syringes and fluid injectors for pressurized injection of fluids, such as a contrast solution (often referred to simply as "contrast"), a flushing agent, such as saline, and other medical fluids have been developed for use in procedures such as angiography, computed tomography (CT), ultrasound, magnetic resonance imaging (MRI), positron emission tomography (PET), and other imaging procedures. In general, these fluid delivery systems are designed to deliver a preset amount of fluid at a desired flow rate.

An actual flow rate (or delivered volume) of fluid that is delivered to the patient is targeted to be as close as possible to the desired flow rate (or desired volume). However, the actual performance of the fluid delivery system is a function of many factors due to overall impedance, compliance, and capacitance of the fluid delivery system. In certain delivery procedures, impedance, compliance, and capacitance of the fluid delivery system may cause a fluid flow over-rate or under-rate (or volume over- or under-delivery) from a desired flow rate (or desired volume).

As a result, existing approaches fail to address the under-delivery or over-delivery of fluid resulting from system impedance, compliance, and/or capacitance. As a result, less than optimal injection boluses may result and/or operation of the fluid delivery system can result in relatively large amounts of wasted fluid, and/or under-delivery of fluid to a patient.

Accordingly, there is a need in the art for improved calibration of the fluid injector to better ensure that a desired volume of fluid is delivered to a patient at a desired flow rate. There is a further need for improved systems and methods for calibrating a fluid injector, as well as systems and methods for characterizing the performance of a fluid delivery system and correlating the desired performance with actual performance in terms of fluid flow rate and volume delivered.

BRIEF SUMMARY

In some examples of the present disclosure, an improved system and method for calibrating the volume of fluid to be delivered to a patient in an injection procedure is disclosed. In examples according to the present disclosure, a method of correcting for inaccuracies in a volume of fluid delivered to a patient due to impedance, compliance, and/or capacitance is disclosed. This system and method address sources of error in delivered fluid volume. In certain embodiments, the present system and methods may be applied to fluid injectors comprising stopcocks or other shut off features to isolate a pressurized fluid filled syringe from a patient during an injection protocol.

In examples according to the present disclosure, a system and method are presented that allows for sources of error due to impedance, compliance, and/or capacitance in the injector system (such as in injector components, disposable components, syringes, etc.) and predicts the over-delivered or under-delivered volume based thereon.

According to a first embodiment, the present disclosure provides methods for correcting a volume of fluid delivered by a fluid injector system during an injection procedure using one or more fluid reservoir. The method may comprise determining a fluid volume of a first fluid in at least one fluid reservoir of the fluid injector system; determining a pressure at which a first programmed volume of the first fluid is to be injected; determining a system volume compliance according to Equation (1) for at least one of the at least one fluid reservoir, one or more fluid injector mechanical components associate with the at least one fluid reservoir, and one or more tubing system components;

$$C_1 = A_1 \cdot V_1 + B_1 \cdot P_1 + O_1 \tag{1}$$

predicting a volume compliance factor of fluid in the at least one fluid reservoir according to Equation (2), $$VC_1 = PV_1 + C_1 \tag{2}$$

and compensating for the volume compliance factor to deliver a programmed fluid volume by one of over-driving a distance that the drive member travels in the at least one fluid reservoir, under-driving the distance that the drive member travels in the at least one fluid reservoir, increasing a delivery time of the fluid in the at least one fluid reservoir, and decreasing the delivery time of the fluid in the at least one fluid reservoir. Referring to Equation (1), $C_1$ is the system volume compliance of the at least one fluid reservoir, $A_1$ is a position scalar of the at least one fluid reservoir, $V_1$ is available volume of the at least one fluid reservoir, $B_1$ is a pressure constant of the at least one fluid reservoir, $P_1$ is a pressure of fluid within the at least one fluid reservoir, and $O_1$ is the compensation factor of the at least one fluid reservoir. Referring to Equation (2), $VC_1$ is the volume compliance factor of the fluid in the at least one fluid reservoir, $PV_1$ is the programmed volume of the first fluid, and $C_1$ is the system volume compliance of the at least one fluid reservoir.

According to specific embodiments, the system compliance volume of Equation (1) is determined according to Equation (3) as follows:

$$z^{-1} = c \cdot y^{0.5} + b/x^{0.5} + a \tag{3}$$

where z is the system volume compliance (C), c is the position scalar (A), y is the available volume in the at least one fluid reservoir ($V_1$), b is the pressure constant (B), x is the pressure of the fluid with the at least one fluid reservoir ($P_1$), and a is the compensation factor (O). In specific embodiments, a has a value ranging from 0.112 to 0.115, b has a value ranging from 10.35 to 10.45, and c has a value ranging from −0.01465 to −0.01495. In a specific embodiment, c=−0.014863432, b=10.39086, and a=0.11422056.

In examples according to the present disclosure, the method disclosed may be stored on memory, controlled by a processor, and carried out automatically whenever an injection protocol is initiated. According to other examples, this method may be carried out at the prompting of a user.

According to another embodiment, the present disclosure provides a fluid delivery system capable of carrying out any of the various methods described herein. In certain embodiments, the fluid delivery system comprises a fluid injector; at least one first fluid reservoir configured to contain a first fluid; at least one first drive member configured to drive fluid from the at least one first fluid reservoir; and a controller in operable communication with the at least one first drive member.

The controller in various embodiments comprises computer readable memory containing instructions that, when executed by the controller, causes the controller to: determine a fluid volume of a first fluid in at least one fluid reservoir of the fluid injector system; determine a pressure at which a first programmed volume of the first fluid is to be injected; determine a system volume compliance according to Equation (1) for at least one of the at least one fluid reservoir, one or more fluid injector mechanical components associate with the at least one fluid reservoir, and one or more tubing system components:

$$C_1 = A_1 \cdot V_1 + B_1 \cdot P_1 + O_1 \quad (1)$$

where $C_1$ is the system volume compliance of the at least one fluid reservoir, $A_1$ is a position scalar of the at least one fluid reservoir, $V_1$ is available volume of the at least one fluid reservoir, $B_1$ is a pressure constant of the at least one fluid reservoir, $P_1$ is a pressure of fluid within the at least one fluid reservoir, and $O_1$ is the compensation factor of the at least one fluid reservoir; predict a volume compliance factor of fluid in the at least one fluid reservoir according to Equation (2):

$$VC_1 = PV_1 + C_1 \quad (2)$$

where $VC_1$ is the volume compliance factor of the fluid in the at least one fluid reservoir, $PV_1$ is the programmed volume of the first fluid, and $C_1$ is the system volume compliance of the at least one fluid reservoir; and compensate for the volume compliance factor to deliver a programmed fluid volume by one of over-driving a distance that a drive member travels in the at least one fluid reservoir, under-driving a distance that the drive member travels in the at least one fluid reservoir, increasing a delivery time of the fluid in the at least one fluid reservoir, and decreasing the delivery time of the fluid in the at least one fluid reservoir.

According to the present disclosure, a capacitance check may be performed at various times during the filling or expelling fluid from the syringe or syringes. A capacitance check or measurement may be conducted in real time, and for each injection, or at selected times during an injection to ensure accurate fluid volume delivery during an injection protocol.

Examples of the system and method according to the present disclosure may be used to determine the volume of fluid trapped in an injector system with active control after a stopcock is closed.

It is to be understood that the volume inaccuracy discussed herein—i.e., the under-delivery of fluid due to impendence, compliance, or capacitance characteristics of the fluid injector and/or medical fluid—is a condition generally associated with "closed" systems, or systems with active control, such as those discussed with respect to FIG. 5. Thus, the correction discussed herein, an example of which is discussed in connection to at FIGS. 9 and 10A-10D, is particularly applicable to such injector systems.

Various aspects of the system and method for injector position calibration of the fluid injector are disclosed in one or more of the following numbered clauses:

Clause 1. A method for correcting a volume of fluid delivered by a fluid injector system during an injection procedure using one or more fluid reservoir, the method comprising: determining a fluid volume of a first fluid in at least one fluid reservoir of the fluid injector system; determining a pressure at which a first programmed volume of the first fluid is to be injected; determining a system volume compliance according to Equation (1) for at least one of the at least one fluid reservoir, one or more fluid injector mechanical components associate with the at least one fluid reservoir, and one or more tubing system components:

$$C_1 = A_1 \cdot V_1 + B_1 \cdot P_1 + O_1 \quad (1)$$

where $C_1$ is the system volume compliance of the at least one fluid reservoir, $A_1$ is a position scalar of the at least one fluid reservoir, $V_1$ is available volume of the at least one fluid reservoir, $B_1$ is a pressure constant of the at least one fluid reservoir, $P_1$ is a pressure of fluid within the at least one fluid reservoir, and $O_1$ is the compensation factor of the at least one fluid reservoir; predicting a volume compliance factor of fluid in the at least one fluid reservoir according to Equation (2)

$$VC_1 = PV_1 + C_1 \quad (2)$$

where $VC_1$ is the volume compliance factor of the fluid in the at least one fluid reservoir, $PV_1$ is the programmed volume of the first fluid, and $C_1$ is the system volume compliance of the at least one fluid reservoir; and compensating for the volume compliance factor to deliver a programmed fluid volume by one of over-driving the distance that the drive member travels in the at least one fluid reservoir, under-driving the distance that the drive member travels in the at least one fluid reservoir, increasing a delivery time of the fluid in the at least one fluid reservoir, and decreasing the delivery time of the fluid in the at least one fluid reservoir.

Clause 2. The method of clause 1, wherein the at least one fluid reservoir comprises at least one first fluid reservoir containing the first fluid and at least one second fluid reservoir containing a second fluid, wherein the method further comprises: determining a fluid volume of the second fluid in at least one second fluid reservoir of the fluid injector system; determining a second pressure at which a programmed volume of the second fluid is to be injected; determining a system volume compliance according to Equation (1) for the at least one second fluid reservoir, one or more fluid injector mechanical components associated with the second reservoir, and one or more tubing system components:

$$C_2 = A_2 \cdot V_2 + B_2 \cdot P_2 + O_2 \quad (1)$$

where $C_2$ is the system volume compliance for the at least one second fluid reservoir, $A_2$ is a position scalar for the at least one second fluid reservoir, $V_2$ is available volume for the at least one second fluid reservoir, $B_2$ is a pressure constant for the at least one second fluid reservoir, $P_2$ is a pressure of fluid within the at least one second fluid reservoir, and $O_2$ is the compensation factor for the at least one second fluid reservoir; predicting a volume compliance factor of fluid in the at least one second reservoir according to Equation (2)

$$VC_2 = PV_2 + C_2 \quad (2)$$

where $VC_2$ is the volume compliance factor of the at least one second fluid reservoir, $PV_2$ is the programmed volume the at least one second fluid reservoir, and $C_2$ is the system volume compliance the at least one second fluid reservoir; and compensating for the volume compliance factor the at least one second fluid reservoir to deliver a programmed fluid volume of the second fluid by one of over-driving the distance that the drive member travels in the at least one second fluid reservoir, under-driving the distance that the drive member travels in the at least one second fluid reservoir, increasing a delivery time of the fluid in the at least one second fluid reservoir, and decreasing the delivery time of the fluid in the at least one second fluid reservoir.

Clause 3. The method of clause 1 or 2, wherein the at least one fluid reservoir comprises at least one first fluid reservoir containing the first fluid, the at least one second fluid reservoir containing the second fluid and at least one third fluid reservoir containing a third fluid.

Clause 4. The method of any one of clauses 1 to 3, further comprising the step of determining whether the at least one fluid reservoir contains at least a volume of fluid corresponding to the programmed volume plus an amount of fluid equal to the system volume compliance according to Equation (1).

Clause 5. The method of any one of clauses 1 to 4, wherein the at least one fluid reservoir, the at least one second fluid reservoir, and the at least one third fluid reservoir are independently selected from the group consisting of a syringe, a rolling diaphragm syringe, a peristaltic pump, and a compressible bag.

Clause 6. The method of any one of clauses 1 to 4, wherein at least one of the at least one fluid reservoir, the at least one second fluid reservoir, and the at least one third fluid reservoir is a syringe.

Clause 7. The method of clause 6, wherein the syringe comprises a plunger operatively connected to a drive member selected from a linear actuated piston and a motor driven piston.

Clause 8. The method of any one of clauses 1 to 4, wherein at least one of the at least one fluid reservoir, the at least one second fluid reservoir, and the at least one third fluid reservoir is a rolling diaphragm syringe.

Clause 9. The method of clause 8, wherein a proximal end of the rolling diaphragm syringe is operatively connected to a drive member selected from a linear actuated piston and a motor driven piston.

Clause 10. The method of any one of clauses 6 to 9, the system compliance volume of Equation (1) is determined according to Equation (3) as follows:

$$z^{-1} = c \cdot y^{0.5} + b/x^{0.5} + a \qquad (3)$$

where z is the system volume compliance (C), c is the position scalar (A), y is the available volume in the at least one fluid reservoir ($V_1$) b is the pressure constant (B), x is the pressure of the fluid with the at least one fluid reservoir ($P_1$), and a is the compensation factor (O).

Clause 11. The method of clause 10, wherein wherein a has a value ranging from 0.112 to 0.115, b has a value ranging from 10.35 to 10.45, and c has a value ranging from $-0.01465$ to $-0.01495$.

Clause 12. The method of any one of clauses 1 to 11, wherein compensating for the volume compliance factor the at least one fluid reservoir comprises: over-driving the distance that the drive member travels in the at least one fluid reservoir; and injecting an addition volume of the first fluid equal to the volume compliance factor.

Clause 13. The method of clause 12, further comprising closing a valve to fluidly isolate the at least one fluid reservoir from the patient after injecting the additional volume of the first fluid.

Clause 14. The method of any one of clauses 1 to 11, wherein compensating for the volume compliance factor of the at least one fluid reservoir comprises increasing a delivery time of the first fluid in the at least one fluid reservoir.

Clause 15. The method of clause 14, wherein increasing the delivery time of the first fluid comprises increasing the delivery time by an amount sufficient to deliver an additional volume of the first fluid equal to the volume compliance factor.

Clause 16. The method of any one of clauses 1 to 15, further comprising reporting to a user a value corresponding to corrected volume of a fluid being delivered to the patient from the at least one fluid reservoir, wherein the corrected volume accounts for the programmed volume and the system volume compliance.

Clause 17. A fluid delivery system comprising: a fluid injector; at least one first fluid reservoir configured to contain a first fluid; at least one first drive member configured to drive fluid from the at least one first fluid reservoir; and a controller in operable communication with the at least one first drive member, wherein the controller comprises computer readable memory containing instructions that, when executed by the controller, causes the controller to: determine a fluid volume of a first fluid in at least one fluid reservoir of the fluid injector system; determine a pressure at which a first programmed volume of the first fluid is to be injected; determine a system volume compliance according to Equation (1) for at least one of the at least one fluid reservoir, one or more fluid injector mechanical components associate with the at least one fluid reservoir, and one or more tubing system components:

$$C_1 = A_1 \cdot V_1 + B_1 \cdot P_1 + O_1 \qquad (1)$$

where $C_1$ is the system volume compliance of the at least one fluid reservoir, $A_1$ is a position scalar of the at least one fluid reservoir, $V_1$ is available volume of the at least one fluid reservoir, $B_1$ is a pressure constant of the at least one fluid reservoir, $P_1$ is a pressure of fluid within the at least one fluid reservoir, and $O_1$ is the compensation factor of the at least one fluid reservoir; predict a volume compliance factor of fluid in the at least one fluid reservoir according to Equation (2):

$$VC_1 = PV_1 + C_1 \qquad (2)$$

where $VC_1$ is the volume compliance factor of the fluid in the at least one fluid reservoir, $PV_1$ is the programmed volume of the first fluid, and $C_1$ is the system volume compliance of the at least one fluid reservoir; and compensate for the volume compliance factor to deliver a programmed fluid volume by one of over-driving a distance that the drive member travels in the at least one fluid reservoir, under-driving a distance that the drive member travels in the at least one fluid reservoir, increasing a delivery time of the fluid in the at least one fluid reservoir, and decreasing the delivery time of the fluid in the at least one fluid reservoir.

Clause 18. The fluid delivery system according to clause 17, wherein the controller is configured to determine the system compliance volume of Equation (1) according to Equation (3) as follows:

$$z^{-1} = c \cdot y^{0.5} + b/x^{0.5} + a \qquad (3)$$

where z is the system volume compliance (C), c is the position scalar (A), y is the available volume in the at least one fluid reservoir ($V_1$) b is the pressure constant (B), x is the pressure of the fluid with the at least one fluid reservoir ($P_1$), and a is the compensation factor (O).

Clause 19. The fluid delivery system of clause 18, wherein a has a value ranging from 0.112 to 0.115, b has a value ranging from 10.35 to 10.45, and c has a value ranging from −0.01465 to −0.01495.

Clause 20. The fluid delivery system of any one of clauses 17 to 19, wherein the computer readable memory containing further instructions that, when executed by the controller, causes the controller to compensate for the volume compliance factor; causes the controller to: over-drive the distance that the drive member travels in the at least one fluid reservoir; and inject an addition volume of the first fluid equal to the volume compliance factor.

Clause 21. The fluid delivery system of any one of clauses 17 to 19, wherein the computer readable memory containing further instructions that, when executed by the controller, causes the controller to compensate for the volume compliance factor; causes the controller to: increase the delivery time of the first fluid in the at least one fluid reservoir by an amount sufficient to deliver an additional volume of the first fluid equal to the volume compliance factor.

These and other features and characteristics of a system and method for correction of errors in fluid delivery of a fluid injector, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only.

DETAILED DESCRIPTION

Figure 1:
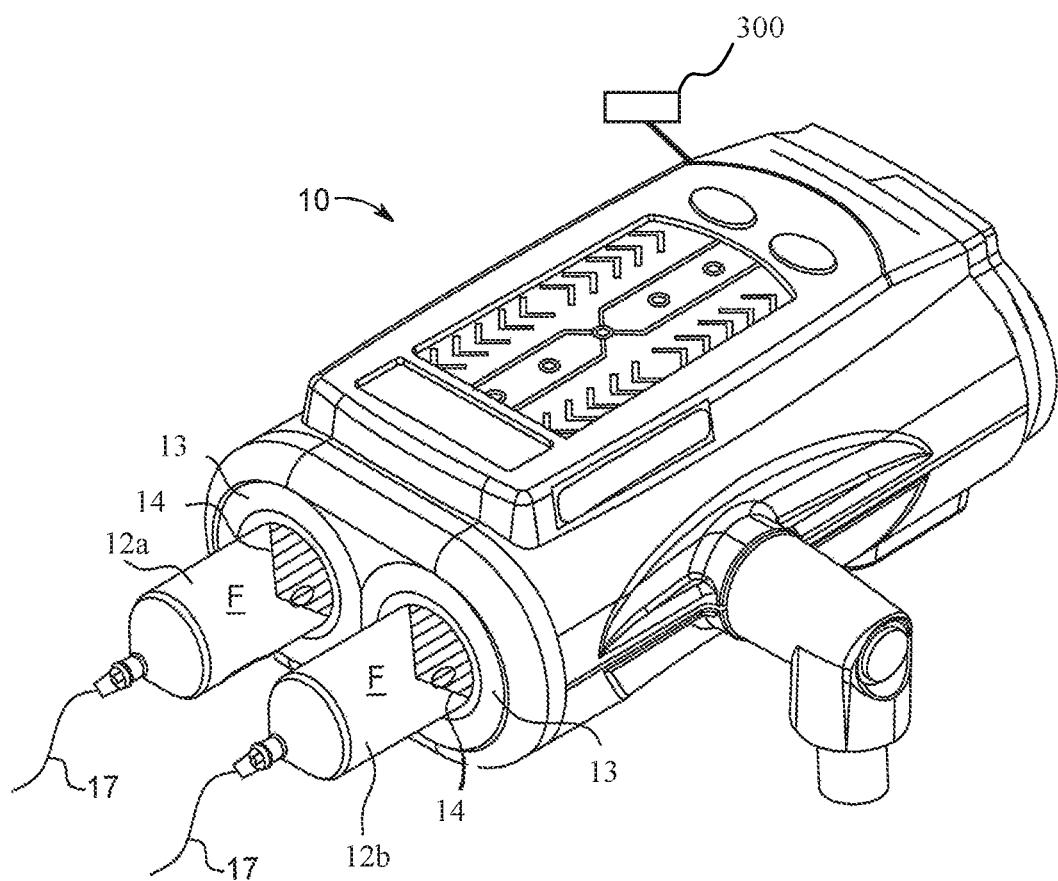
FIG. 1 is a perspective view of a fluid delivery system according to an example of the present disclosure.

As used in the specification and the claims, the singular form of "a", "an", and "the" include plural referents unless the context clearly dictates otherwise.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures.

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". The term "about" means a range of plus or minus ten percent of the stated value.

Unless otherwise indicated, all ranges or ratios disclosed herein are to be understood to encompass any and all subranges or sub-ratios subsumed therein. For example, a stated range or ratio of "1 to 10" should be considered to include any and all subranges between (and inclusive of) the minimum value of 1 and the maximum value of 10; that is, all subranges or sub-ratios beginning with a minimum value of 1 or more and ending with a maximum value of 10 or less, such as but not limited to, 1 to 6.1, 3.5 to 7.8, and 5.5 to 10.

The term "at least" means "greater than or equal to".

The term "includes" is synonymous with "comprises".

When used in relation to a syringe and/or a plunger, the term "proximal" refers to a portion of a syringe and/or a plunger nearest a fluid injector when a syringe and/or a plunger is oriented for connecting to a fluid injector. The term "distal" refers to a portion of a syringe and/or a plunger farthest away from a fluid injector when a syringe and/or a plunger is oriented for connecting to a fluid injector. The term "radial" refers to a direction in a cross-sectional plane normal to a longitudinal axis of a syringe, a plunger, and/or a piston extending between proximal and distal ends. The term "circumferential" refers to a direction around an inner or outer surface of a sidewall of a syringe, a plunger, and/or a piston. The term "axial" refers to a direction along a longitudinal axis of a syringe, a piston, and/or a piston extending between the proximal and distal ends. The term "open" when used to refer to a fluid delivery component means that the system is in fluid connection with an outlet, for example through a nozzle or the open end of a tubing component or catheter. In an open system, fluid flow may be constrained, for example by forcing a fluid through a small diameter fluid path where flow may be determined by physical parameters of the system and the fluid, such as tubing diameter, fluid path constrictions, applied pressure, viscosity, etc. The term "closed" when used to refer to a fluid delivery component means that the system is not in fluid connection with an outlet, for example where fluid flow is stopped by a valve, such as a stopcock, high crack pressure valve, pinch valve, and the like. As used herein the term "slack" means mechanical slack, including a clearance or lost motion in a mechanism caused by gaps between parts, compression of mechanical components under applied load (such as by applied pressure), deflection of mechanical components under applied load (such as by applied pressure), that results in a delay of pressurized delivery of a fluid from a fluid injection after application of force.

It is to be understood that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the examples disclosed herein are not to be considered as limiting.

Characterizing an impedance of a fluid delivery system to minimize a difference between desired and actual fluid delivery system performance requires consideration how energy from an energy source is used in or moves through the system. The energy output or loss from the fluid delivery system may be in the form of heat losses through frictional forces or of work done on the fluid delivery system, or inertial effects. For example, some of the energy carried by the pressurized fluid as it is delivered under pressure through a catheter is lost through resistive, frictional, or dissipative heating of the fluid. Additionally, pressurized delivery of fluid can also increase the potential energy of the system in terms of an increase in overall volume of system components or compressive forces on system components, as discussed herein. Furthermore, the kinetic energy of pressurized fluid moving through the fluid delivery system can affect the overall performance of the fluid delivery system. For example, inertial forces of moving contrast material and expansion of the containers and tubing associated with the system may cause a phase lag between movement of the syringe plunger within the injector syringe and movement of contrast material out of the catheter and into the patient.

Figure 7A:
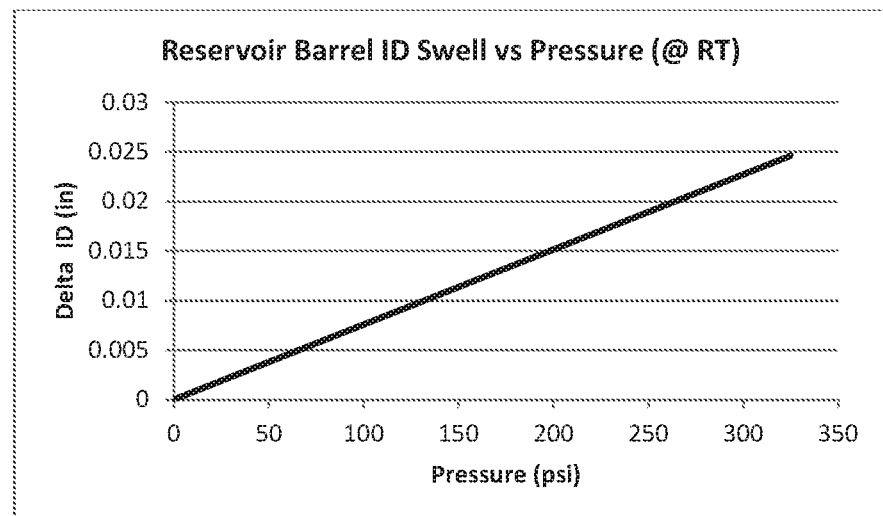
FIG. 7A is a graphical representation for change in the internal diameter of one embodiment of a fluid reservoir as a function of internal fluid pressure.

Due to high injection pressures, which may be on the order of 1,200 psi in some angiographic procedures, there may be an expansion or compression of various components of the fluid delivery system, such as the syringes, tubing connected to the patient, and components of the fluid injector, such that there may be a volume of fluid in the syringe and tubing in excess of the desired quantity selected to be delivered in the injection procedure. Such increase in the quantity of fluid occurs due to system capacitance. Total system capacitance (also referred to as compliance or elasticity) represents the amount of fluid (i.e., change in volume, such as excess volume) that is captured in the swelling, compression, and/or deflection of the components of the fluid delivery system. In general, capacitance is directly correlative to injection pressure and inversely correlative to volume of contrast medium and saline in the syringes. In other words, capacitance increases with an increase in injection pressure and an increase in volume of fluid in the syringes. Total system capacitance is inherent to each fluid delivery system and depends on a plurality of factors beyond pressure and volume of fluid remaining in the system, including, without limitation, injector construction, mechanical properties of materials used to construct the syringe, plunger, pressure jacket surrounding the syringe, and fluid lines delivering the fluid to the patient, size of the syringe, plunger, pressure jacket, diameter of tubing or other orifices through which the fluid must pass under pressure, presence of valves, such as high crack pressure valves, stopcocks, or pinch valves, and fluid properties, such as temperature, viscosity, and density. For example, as illustrated in FIG. 7A, the inner diameter of a syringe filled with a fluid expands, as shown by the Delta ID, as the pressure applied to the fluid increases. This change in inner diameter, in part, leads to a compliance volume that may not be delivered during a fluid injection, leading to injection volume inaccuracies. However, this analytical approach shown in FIG. 7A represents only one component of ompliance volume and may not readily take into account the axial stretching of the reservoir, the compression of the plunger, or the deflection of the load bearing components of the system. Therefore according to certain embodiments, an empirical approach taking measured values for multiple pressure, volume, and compliance points may be taken and the compliance of the system may be plotted and an equation representing the system compliance may be determined.

Figure 7B:
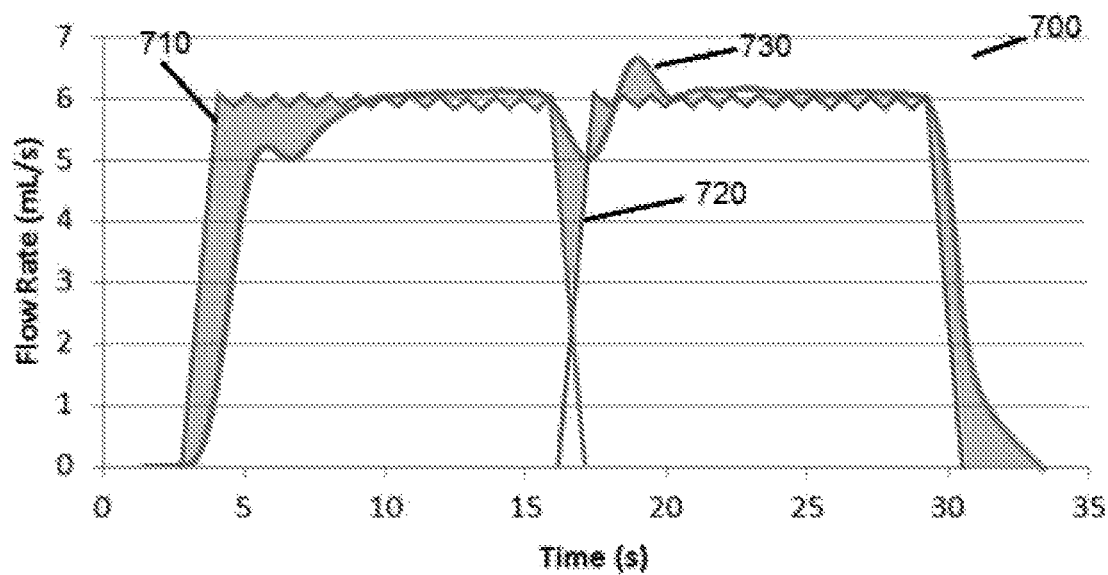
FIG. 7B is a graphical representation of the expected flow profile compared to the actual profile for a fluid injection undergoing compliance volume expansion.
Figure 8A:
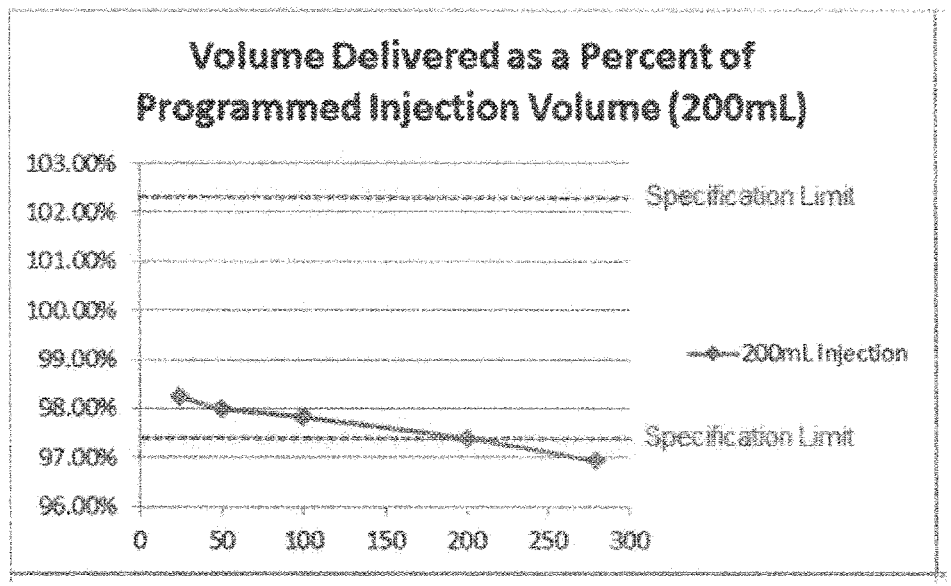
FIG. 8A is a graph showing percentage of fluid delivery from a 200 milliliter (mL) volume as a function of pressure for an exemplary single-container injector system having active control.
Figure 8B:
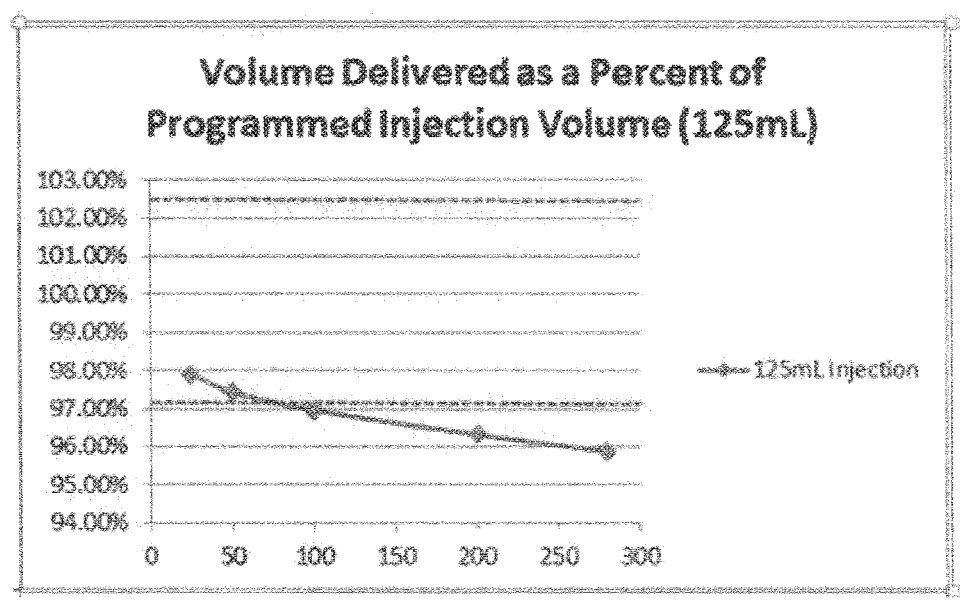
FIG. 8B is a graph showing percentage of desired fluid delivered from a 125 milliliter (mL) volume as a function of pressure for an exemplary single-container injector system having active control.
Figure 8C:
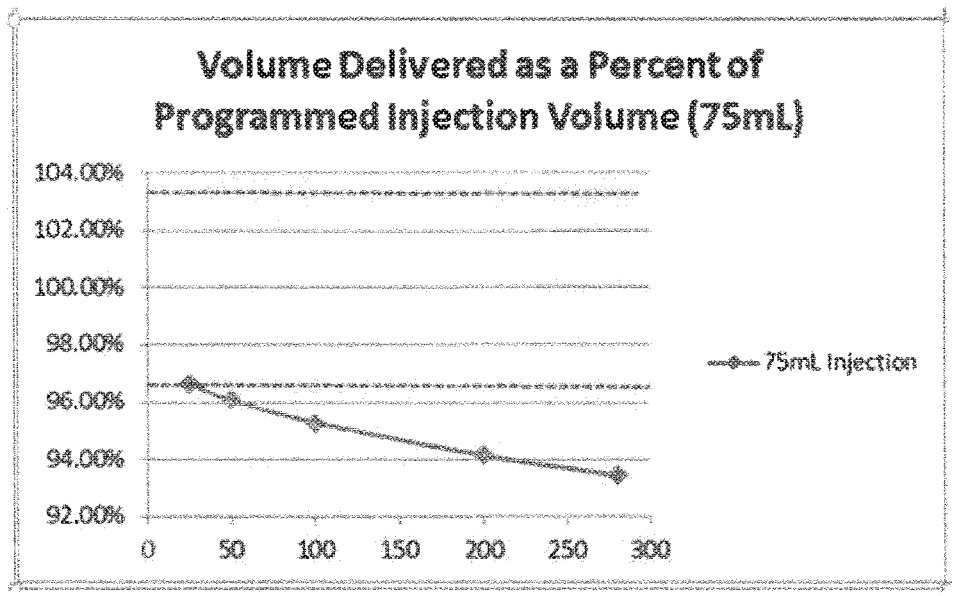
FIG. 8C is a graph showing percentage of desired fluid delivered from a 75 milliliter volume as a function of pressure for an exemplary single-container injector system having active control.
Figure 8D:
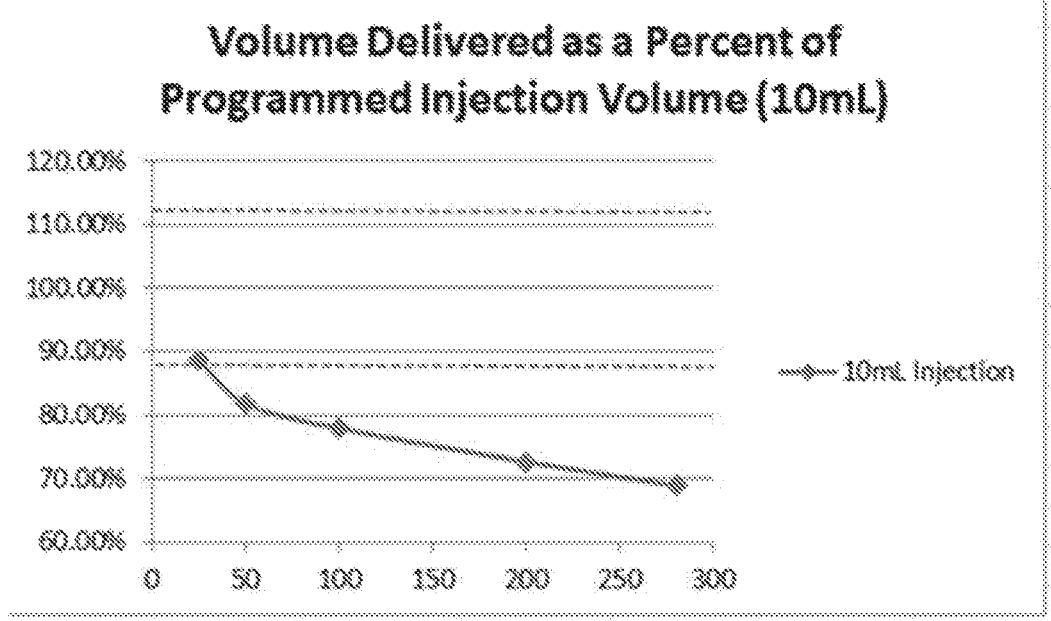
FIG. 8D is a graph showing percentage of desired fluid delivered from a 10 milliliter (mL) volume as a function of pressure for an exemplary single-container injector system having active control.

FIG. 7B illustrates a fluid injection protocol 700 showing a difference in expected flow profile for a first fluid 710 and a second fluid 720, compared to actual flow profiled 730 as measured by a downstream sensor. The difference between the two curves represents the compliance volume which results in volume inaccuracies, for examples per phase volume inaccuracies, unless the compliance volume is returned at the end of an injection (for instance step 730 after a specified time) or it is compensated for according to the embodiments of the methods herein. According to one embodiment, the injector may be programmed to keep a running tally of the delta between the two curves (positive and negative) to generate a net difference corresponding to the dynamic compliance at any given point in time during the injection. This dynamic compliance may be utilized by the processor or controller during a drive volume compensation process, for example by overdriving or underdriving the distance of travel for the drive member associated with the fluid reservoir by an amount sufficient to compensate for the compliance volume, thereby delivering a volume substantially equal to an expected volume that corresponds to the expected flow profiles 710 and 720. According to another embodiment, the measured or calculated dynamic compliance information may be used by the processor or controller to adjust the motor speed and movement of the drive member to generate the desired profiles 710 and 720.

While various approaches exist for characterizing the performance of a fluid delivery system and correlating the desired performance with actual performance, in terms of fluid flow rate and volume delivered, these approaches do not address the differences between desired and actual performance due to impedance and/or capacitance of the fluid delivery system in a comprehensive manner. For example, in some systems that include an active control, such as a stopcock or other device to stop fluid flow to a patient or fluidly isolate the patient at the end of a portion of an injection procedure, a volume of medial fluid actually delivered to the patient may be different from the desired volume due to errors associated with impedance. In examples consistent with this disclosure, the volume programmed to be delivered to the patient may be less than the desired volume because capacitance volume taken up by the syringes is not delivered, for example, due to it being isolated by closure of a stopcock or other valve or by stopping the injection at the programmed volume value that does not incorporate the capacitance volume.

In some examples of the present disclosure, an improved system and method for calibrating the volume of fluid to be delivered to a patient in an injection procedure is disclosed. In examples according to the present disclosure, a method of correcting for inaccuracies in a volume of fluid delivered to a patient due to impedance and/or capacitance is disclosed. This system and method address sources of error in delivered fluid volume. In certain embodiments, the present system and methods may be applied to fluid injectors comprising stopcocks or other shut off features to isolate a pressurized fluid filled syringe from a patient during an injection protocol.

According to certain embodiment, the present disclosure provides methods for correcting a volume of fluid delivered by a fluid injector system during an injection procedure using one or more fluid reservoir. The methods may correct for fluid volume inaccuracies during an injection protocol due, at least in part, to lost injection volumes as a results of system compliance, such a mechanical slack associated with motor and drive member components under a force load as a result of pressurization of a fluid reservoir; deflection of various injector components, drive members, and syringe components due to the force load and strain, and compliance associated with fluid containing components which may hydraulically swell under the applied forces. As a fluid reservoir dispenses a programmed volume of a medical fluid under pressures associated with various injections of imaging contrast agents, saline, and/or other medical fluids, the applied pressures result in at least a portion of the fluid volume of the syringe being converted into a compliance volume that is not accounted for in the programmed volume of the injection and therefor may not be injected into the patient resulting in under delivery of the fluid or may result in over delivery of fluid as the compliance volume is released when the pressure load force is released. The various systems and methods described herein provide increased fluid delivery accuracies by accounting for the compliance volume in the form of one of over-driving the distance that the drive member travels in the fluid reservoir resulting in delivery of the programmed volume and an extra volume of fluid substantially equal to the compliance volume, under-driving the distance that the drive member travels in the fluid reservoir resulting in delivery of a fluid volume equal to the programmed volume less the compliance volume, increasing a delivery time of the fluid in the fluid reservoir by a time necessary to allow delivery of the desired volume, and decreasing the delivery time of the fluid in the fluid reservoir to avoid over delivery of the fluid over the desired volume. Medical fluids that may be injected using the presently disclosed methods include, without limitation, imaging contrast media, such as for CT, CV, MR, or PET contrast media, saline, or other medical fluids for which accurate fluid delivery volumes are desired.

The volume associated with the capacitance, compliance, and/or impedance associated with a pressurized fluid reservoir may depend on a number of factors, such as inherent system slack, fluid type, fluid viscosity, reservoir configuration, such as diameter, volume, material, and outlet parameters, fluid volume in the reservoir, applied pressure load, etc. According to various embodiments, a processor may utilize one or more of these factors to determine or predict the system volume compliance of a fluid delivery system and the fluid reservoir components.

The method may comprise determining a fluid volume of a first fluid in at least one fluid reservoir of the fluid injector system; determining a pressure at which a first programmed volume of the first fluid is to be injected; determining a system volume compliance according to Equation (1) for at least one of the at least one fluid reservoir, one or more fluid injector mechanical components associate with the at least one fluid reservoir, and one or more tubing system components;

$$C_1 = A_1 \cdot V_1 + B_1 \cdot P_1 + O_1 \qquad (1)$$

predicting a volume compliance factor of fluid in the at least one fluid reservoir according to Equation (2), $$VC_1 = PV_1 + C_1 \qquad (2)$$

and compensating for the volume compliance factor to deliver a programmed fluid volume by one of over-driving the distance that the drive member travels in the at least one fluid reservoir, under-driving the distance that the drive member travels in the at least one fluid reservoir, increasing a delivery time of the fluid in the at least one fluid reservoir, and decreasing the delivery time of the fluid in the at least one fluid reservoir. Referring to Equation (1), $C_1$ is the system volume compliance of the at least one fluid reservoir, $A_1$ is a position scalar of the at least one fluid reservoir, $V_1$ is available volume of the at least one fluid reservoir, $B_1$ is a pressure constant of the at least one fluid reservoir, $P_1$ is a pressure of fluid within the at least one fluid reservoir, and $O_1$ is the compensation factor of the at least one fluid reservoir. Referring to Equation (2), $VC_1$ is the volume compliance factor of the fluid in the at least one fluid reservoir, $PV_1$ is the programmed volume of the first fluid, and $C_1$ is the system volume compliance of the at least one fluid reservoir.

In other embodiments, the fluid injector may be a multi-reservoir fluid injector comprising two, three, or even more fluid reservoirs configured for injecting one or more medical fluids. For example, in certain embodiments, the fluid injector may comprise at least one first fluid reservoir containing the first fluid and at least one second fluid reservoir containing a second fluid. According to these embodiments, the method may further comprise having the processor correct for the fluid volume delivery of the second fluid form the second fluid reservoir. According to these injectors, an injection protocol may comprise sequential injection of the first and second fluids and/or may be capable of a dual flow injection protocol where a specified ratio of the first and second fluids are injected as a mixture. Medical fluids that may be injected using the presently disclosed methods include, without limitation, imaging contrast media, such as for CT, CV, MR, or PET contrast media, saline, or other medical fluids for which accurate fluid delivery volumes are desired. The methods may include determining a fluid volume of the second fluid in at least one second fluid reservoir of the fluid injector system; determining a second pressure at which a programmed volume of the second fluid is to be injected; determining a system volume compliance according to Equation (1) for the at least one second fluid reservoir, one or more fluid injector mechanical components associated with the second reservoir, and one or more tubing system components:

$$C_2 = A_2 \cdot V_2 + B_2 \cdot P_2 + O_2 \quad (1)$$

where $C_2$ is the system volume compliance for the at least one second fluid reservoir, $A_2$ is a position scalar for the at least one second fluid reservoir, $V_2$ is available volume for the at least one second fluid reservoir, $B_2$ is a pressure constant for the at least one second fluid reservoir, $P_2$ is a pressure of fluid within the at least one second fluid reservoir, and $O_2$ is the compensation factor for the at least one second fluid reservoir; predicting a volume compliance factor of fluid in the at least one second reservoir according to Equation (2)

$$VC_2 = PV_2 + C_2 \quad (2)$$

where $VC_2$ is the volume compliance factor of the at least one second fluid reservoir, $PV_2$ is the programmed volume the at least one second fluid reservoir, and $C_2$ is the system volume compliance the at least one second fluid reservoir; and compensating for the volume compliance factor the at least one second fluid reservoir to deliver a programmed fluid volume of the second fluid by one of over-driving the distance that the drive member travels in the at least one second fluid reservoir, under-driving the distance that the drive member travels in the at least one second fluid reservoir, increasing a delivery time of the fluid in the at least one second fluid reservoir, and decreasing the delivery time of the fluid in the at least one second fluid reservoir.

Figure 6:
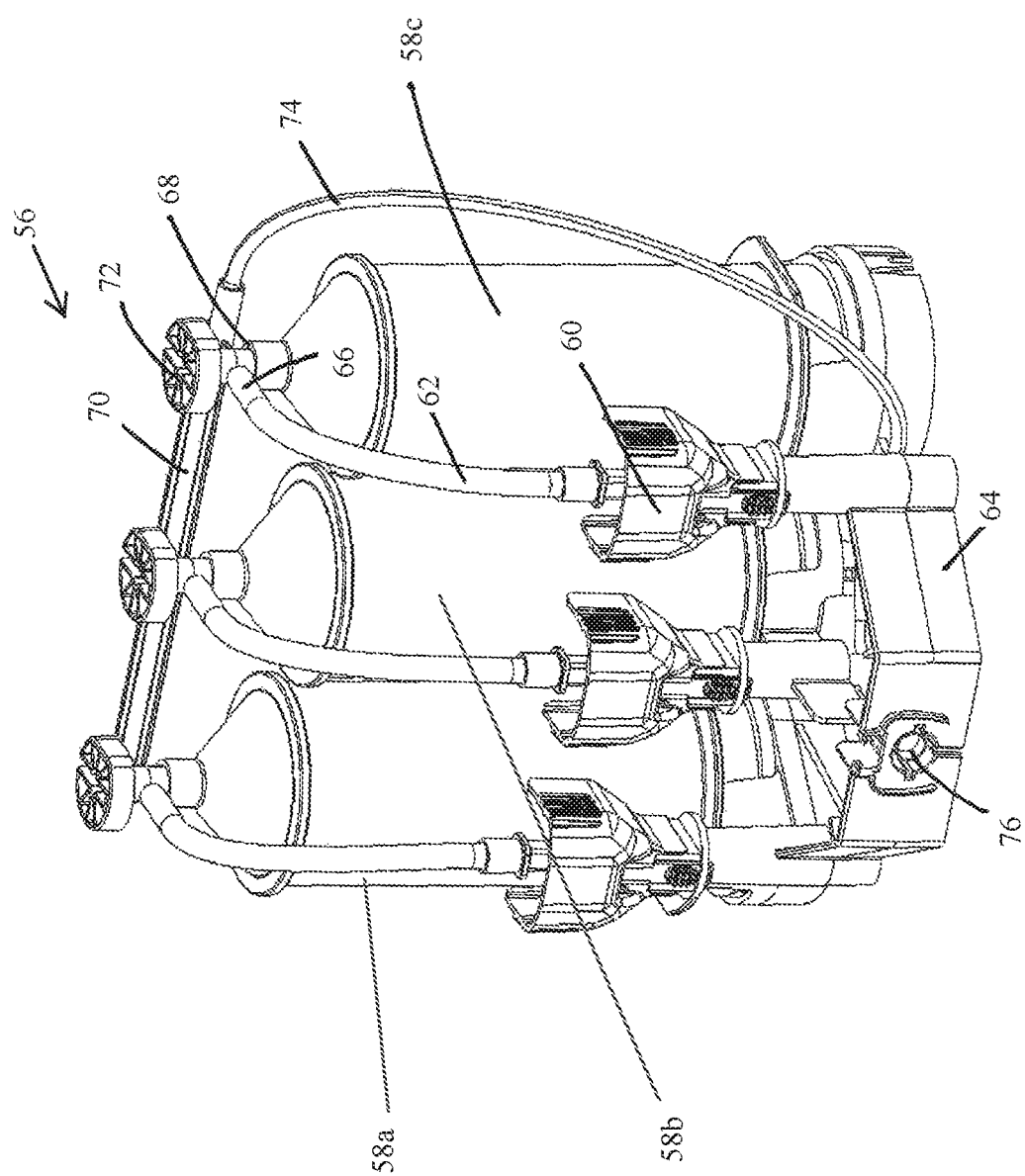
FIG. 6 is a front perspective view of a multi-use disposable system configured for use with the fluid delivery system of FIG. 5.

According to other embodiments, the fluid injector may include at least one first fluid reservoir containing the first fluid, the at least one second fluid reservoir containing the second fluid and at least one third fluid reservoir containing a third fluid, such as illustrated in FIG. 6. The fluid reservoirs according to the various embodiments of the fluid injectors may independently be a syringe, a rolling diaphragm syringe, a peristaltic pump, and a compressible bag. In specific embodiments, the fluid injector may be configured to have a first fluid reservoir and a second fluid reservoir, wherein at least one of the first fluid reservoir and the second fluid reservoir is a syringe. In various embodiments, the first fluid reservoir may be a first syringe and the second fluid reservoir may be a second syringe. In embodiments comprising a third fluid reservoir, the third fluid reservoir may also be a syringe. One or more of the syringes according to various embodiments may be initially empty of any fluid or in other embodiments, one or more of the syringes may be a prefilled syringe.

In embodiments where the fluid injector comprises at least one syringe, the syringe may include a plunger operatively connected to at least one drive member, such as a piston, of the injector. The drive member may be reciprocally operated by one or more of a linear actuator or a motor.

In other embodiments, the fluid injector may be configured to have a first fluid reservoir and a second fluid reservoir, wherein at least one of the first fluid reservoir and the second fluid reservoir is a rolling diaphragm syringe. In specific embodiments, the first fluid reservoir may be a first rolling diaphragm syringe and the second fluid reservoir may be a second rolling diaphragm syringe. In embodiments comprising a third fluid reservoir, the third fluid reservoir may also be a rolling diaphragm syringe. One or more of the rolling diaphragm syringes according to various embodiments may be initially empty of any fluid or in other embodiments, one or more of the rolling diaphragm syringes may be a prefilled rolling diaphragm syringe.

In embodiments where the fluid injector comprises at least one rolling diaphragm syringe, the fluid injector may include at least one drive member, such as a piston, that is configured to releasably engage a proximal end wall of the rolling diaphragm. The drive member may be reciprocally operated by one or more of a linear actuator or a motor to draw in and expel a fluid from the at least one rolling diaphragm syringe.

In embodiments where the fluid injector comprises at least one peristaltic pump, the peristaltic pump may include a roller operatively connected to a drive member, such as a rotary motor. The drive member may be rotated by the motor to rotate the roller of the peristaltic pump to impel the fluid from the fluid reservoir through the fluid path to the patient.

In embodiments where the fluid injector comprises at least one compressible bag, the compressible bag may be compressed, for example by a clam shell or other compressing member to expel the fluid contained within the compressible bag. In various embodiments, the geometry of the compressing member may be modulated or controlled to expel more or less fluid depending on the amount of compliance associated with the bag to achieve accurate volume delivery.

According to various embodiments of the methods described herein may further include the step of determining whether the at least one fluid reservoir contains at least a volume of fluid corresponding to the programmed volume plus an amount of fluid equal to the system volume compliance according to Equation (1). According to these embodiments, the processor may determine whether the fluid reservoir has sufficient fluid volume to deliver the desired volume of the fluid, i.e., a volume equal to the programmed volume plus the fluid volume associated with the system volume compliance, as calculated by Equation (1). For example, if the processor determines that there is sufficient fluid volume for delivery of the desired volume, then the processor may instruct the injector to proceed with the injection. However, if the processor determines that there is not sufficient volume to provide the desired volume, when accounting for the system volume compliance, the processor may provide an alert to the user to warn that the reservoir does not contain sufficient fluid. Alternatively, the processor may instruct the injector in draw in additional fluid into the fluid reservoir so that sufficient volume is present to accurately provide the desired volume. In other embodiments, the 0 mL position may be determine and may reduce or eliminate the need to have the programmed volume plus the compliance factor.

According to various embodiments for example where the injector includes fluid reservoirs that may be selectively closed and fluidly isolated from the fluid path and/or other fluid reservoirs during a multi-fluid delivery process and/or a dual flow fluid delivery process, the system compliance may comprise factors associated with phase compliance and stored compliance. As used herein, "phase compliance" means the dynamic compliance associated with a fluid delivery process during the fluid injection where the reservoir is in fluid communication with the fluid path. For example, as an open fluid reservoir is pressurized, compliance in the system builds up and affects the volume of fluid delivered from the fluid reservoir during the fluid delivery process. As used herein, "stored compliance" means compliance that is stored in a fluid delivery process after the fluid reservoir is closed and fluidly isolated. For example, if a fluid reservoir is pressurized to deliver a first fluid, the fluid reservoir will have a phase compliance which will be converted to a stored compliance when the fluid reservoir is fluidly isolated, for example by closing a valve. The stored compliance in the fluidly isolated fluid reservoir will be reconverted to phase compliance when the fluid reservoir is placed in fluid communication with the fluid path, for example by opening the valve. Alternatively in a dual flow operation where fluid from a first reservoir and a second fluid from a second reservoir are being delivered together, that stored compliance in the first and second fluid reservoirs may individually contribute to the phase compliance of the dual flow fluid mixture, which may also include accounting form pressure equalization between the two fluid reservoirs during the dual flow process.

The processor may utilize Equation (4) when accounting for phase compliance and stored compliance to determine the target volume delivery (as measured by piston position in a syringe system) in a single phase system (i.e., flow of one fluid from a fluid reservoir) as follows:

$$\text{Target position} = \text{staring position} - PV + SC - PC \quad (4)$$

where Target position is the calculated end position of the drive member, starting position is the initial position of the drive member, $PV$ is the programmed volume, $SC$ is the stored compliance, and $PC$ is the phase compliance. Alternatively, for a dual flow injection process the processor may utilize Equation (5) when accounting for phase compliance and stored compliance to determine the target volume delivery for each fluid reservoir:

$$\text{Target position} = \text{starting position} - (PV \cdot \text{mix percent}) + SC - PC \quad (5)$$

wherein once a first reservoir finishes the fluid injection, the valve is closed and the flow rate of injection of the fluid from the second, remaining reservoir is increased to equal the desired rate for the dual flow injection.

In various embodiments, the method may include the step of reporting to the user a value corresponding to the corrected, actual volume being delivered to the patient from the fluid reservoir. The corrected volume would include the programmed volume and the system compliance volume. The processor can inform the user of the fluid delivery amount according to an empirical calculation as opposed to an estimate based on drive member movement. The value may be provided to the user at any time during the fluid injection process, and may even be dynamically displayed on a display unit connected to the processor so that the user can review the delivered fluid volume at any time, for example if the user pauses the injection process.

According to other embodiment, the present disclosure provides for a fluid delivery system capable of performing the various methods of fluid delivery volume correction described herein. According the certain embodiments, the fluid delivery system would comprise a fluid injector; at least one first fluid reservoir configured to contain a first fluid; at least one first drive member configured to drive fluid from the at least one first fluid reservoir; and a controller in operable communication with the at least one first drive member. In various embodiments, the fluid injector may comprise a second fluid reservoir including a second drive member in operable communication with the processor, and in still other embodiments, may include at least a third fluid reservoir including a third drive member in operable communication with the processor. The processor may include a controller having computer readable memory that contain instructions to perform the various steps of the methods described in the various embodiments herein, when the instructions are executed by the controller.

Referring to the drawings in which like reference characters refer to like parts throughout the several views thereof, the present disclosure is generally directed to a fluid injector and a system and method for correcting the volume under-delivered to a patient by the fluid injector. Associated disclosure related to capacitance development and issues associated with fluid injection systems is described in PCT International Application No. PCT/US2017/020637, filed 3 Mar. 2017, the disclosure of which is incorporated herein by this reference.

With reference to FIG. 1, a fluid injector 10 (hereinafter referred to as "injector 10"), such as an automated or powered fluid injector, is adapted to interface with and actuate one or more syringes 12 (hereinafter referred to as "syringe 12"), which may be filed with a fluid F, such as contrast media, saline solution, or any desired medical fluid. The injector 10 may be used during a medical procedure to inject the medical fluid into the body of a patient by driving a plunger 14 of each syringe 12 with a drive member, such as piston 19 (shown in FIG. 2), such as linear actuator or a piston element. The injector 10 may be a multi-syringe injector having two, three or more syringes, wherein the several syringes 12 may be oriented in a side-by-side or other relationship and may be separately actuated by respective drive members/pistons 16 associated with the injector 10. In examples with two or more syringes, for example, arranged in a side-by-side or other relationship and filled with two different fluids, the injector 10 may be configured to deliver fluid from one or both of the syringes 12, sequentially or concurrently. According to one embodiment, the fluid injector 10 may be a dual head injector having two syringes 12a and 12b, a first syringe 12a for delivering a contrast media or other medical fluid and a second syringe 12b for delivering saline or other medically approved flushing agent to flush the contrast media to the patient. In other embodiments, the fluid injector 10 may have three syringes 12, a first and second syringe for delivering one or two different contrast media or other medical fluid and a third syringe for delivering saline or other medically approved flushing agent to flush the contrast media to the patient. According to various embodiments, the fluid injector 10 may be configured to deliver the contrast and saline separately (e.g., delivering a specific volume saline over a specific time followed by delivering a specific volume of contrast over a specific time, followed by a second volume of saline over a specified time to flush the contrast media from the tubing into the patient). According to various embodiments, the fluid injector 10 may be configured to deliver the contrast and saline separately or as a mixture (e.g., delivering a specific volume saline over a specific time followed by delivering a specific volume of contrast or a specified ratio of contrast and saline (i.e., in a "dual flow" process) over a specific time, followed by a second volume of saline over a specified time to flush the contrast media from the tubing into the patient). A technician may program a specific injection protocol into the injector (or use a pre-written protocol) to deliver the desired volumes of saline, contrast, specific ratios of contrast and saline mixtures, etc., at a desired flow rate, time, and volume for each solution. The fluid injector 10 may have at least one bulk fluid source (not shown) for filling the syringes 12 with fluid and in certain embodiments, the fluid injector 10 may have a plurality of bulk fluid source, one for each of the plurality of syringes, for filling each of the plurality of syringes with the desired fluid.

A fluid path set 17 may be in fluid communication with each syringe 12 to place each syringe in fluid communication with a catheter for delivering the fluid F from each syringes 12 to a catheter (not shown) inserted into a patient at a vascular access site. In certain embodiments, fluid flow from the one or more syringes 12 may be regulated by a fluid control module (not shown) that operates various drive members, valves, stopcocks, and flow regulating structures to regulate the delivery of the saline solution and contrast to the patient based on user selected injection parameters, such as injection flow rate, duration, total injection volume, and ratio of fluids from the syringes 12, including specific ratios of each fluid in a dual flow injection protocol.

Figure 2:
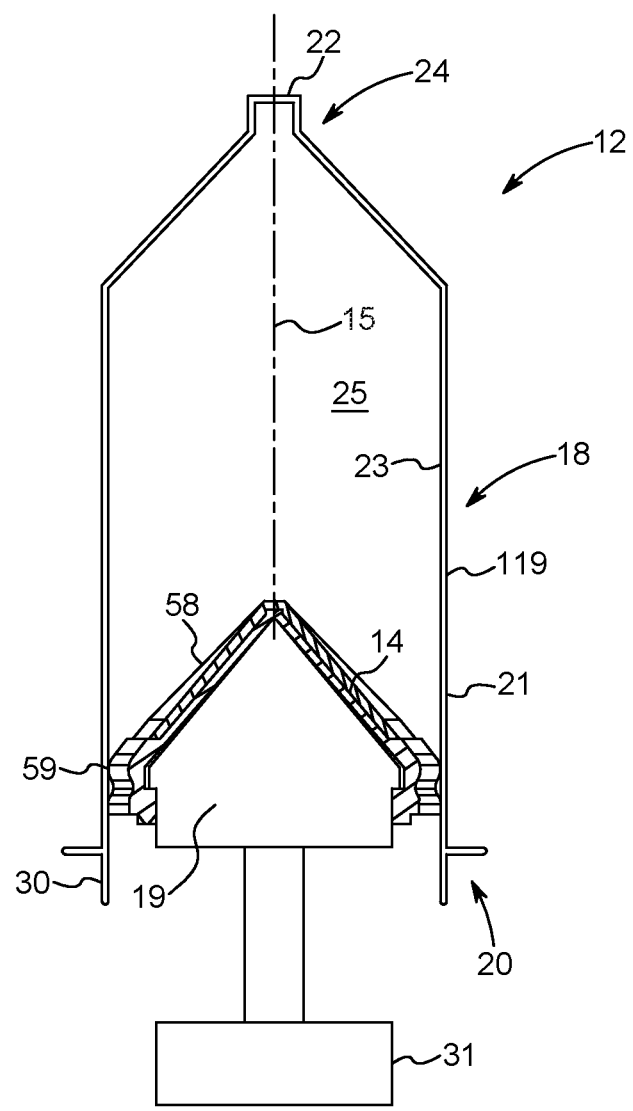
FIG. 2 is a side cross-sectional view of a syringe configured for use with the fluid delivery system of FIG. 1.

With reference to FIG. 2, the drive member 19, such as a reciprocally driven piston moved by a motor 31, may be configured to extend into and from the respective syringe port 13 through an opening in the front end of the injector housing. In fluid injector embodiments comprising a plurality of syringes, a separate drive member/piston 19 may be provided for each syringe 12. Each drive member/piston 19 is configured to impart a motive force to at least a portion of the syringe 12, such as the plunger 14 or a distal end of a rolling diaphragm syringe (for example, as described in PCT/US2017/056747; WO 2016/172467; and WO 2015/164783, the disclosures of which are incorporated herein by this reference). The drive member or piston 19 may be reciprocally operable via electro-mechanical drive components such as a ball screw shaft driven by the motor 31, a voice coil actuator, a rack-and-pinion gear drive, a linear motor, a linear actuator, and the like. The motor 31 may be an electric motor.

Examples of suitable front-loading fluid injectors 10 are disclosed in U.S. Pat. Nos. 5,383,858; 7,553,294; 7,666,169; 9,173,995; 9,199,033; and 9,474,857; and in PCT Application Publication No. WO 2016/191485 and WO 2016/112163, the disclosures of which are incorporated by reference in their entirety.

Having described the general structure and function of specific embodiments of the fluid injector 10, an embodiment of syringe 12 configured for use with the injector 10 will now be described with reference to FIG. 2. The syringe 12 generally has a cylindrical syringe barrel 18 formed from glass, metal, or a suitable medical-grade plastic, desirably a clear or substantially translucent plastic material. The material of the syringe 12 is desirably selected to meet the required tensile and planar stress requirements, water vapor transmission, and chemical/biological compatibility. The barrel 18 has a proximal end 20 and a distal end 24, with a sidewall 119 extending therebetween along a length of a longitudinal axis 15 extending through a center of the barrel 18. In some examples, the distal end 24 may have a conical shape that narrows in a distal direction from the cylindrical barrel 18. A nozzle 22 extends from the distal end 24. The barrel 18 has an outer surface 21 and an inner surface 23 with an interior volume 25 configured for receiving the fluid therein. The proximal end 20 of the barrel 18 may be sealed with the plunger 14 that is reciprocally movable through the barrel 18 by reciprocal movement of the corresponding piston 19 or drive member. The plunger 14 forms a liquid-tight seal against the inner surface 23 of the barrel 18 as the plunger 14 is advanced moved through the barrel 18.

In some examples, the proximal end 20 of the syringe 12 can be sized and adapted for being removably inserted in a syringe port 13 of the injector 10 (shown in FIG. 1). In some examples, the proximal end 20 of the syringe 12 defines an insertion section 30 that is configured to be removably inserted into the syringe port 13 of the injector 10 while the remaining portion of the syringe 12 remains outside of the syringe port 13.

Figure 3:
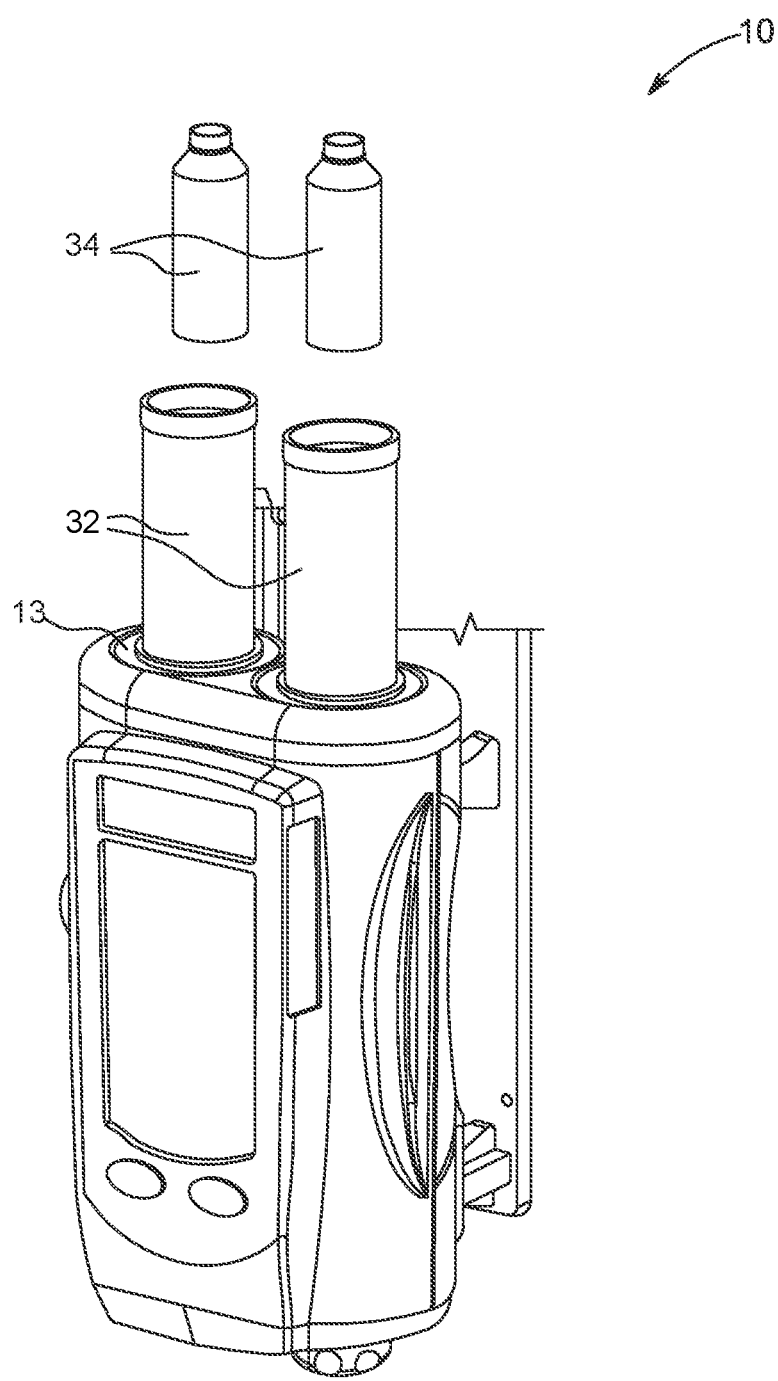
FIG. 3 is a perspective view of a fluid delivery system according to another example of the present disclosure.

In some examples, such as shown in FIG. 3, the injector 10 may be configured for receiving and retaining a pressure jacket 32 within each syringe port 13 of the injector 10. While FIGS. 1 and 3 illustrate fluid injectors 10 with two syringe ports 13, which for the injector 10 shown in FIG. 3 each having a corresponding pressure jacket 32, other examples of the fluid injector 10 may include a single syringe port 13 and optionally, a corresponding pressure jacket 32 or more than two syringe ports 13 with an optional corresponding number of pressure jackets 32. In embodiments comprising pressure jackets, each pressure jacket 32 may be configured to receive a syringe, such as a syringe for an angiographic (CV) procedure, or a rolling diaphragm syringe 34 (suitable examples of which are described in described in PCT/US2017/056747; WO 2016/172467; and WO 2015/164783). A fluid path set, similar to the fluid path set 17 shown in FIG. 1, may be fluidly connected with a discharge end of each rolling diaphragm syringe 34 for delivering fluid from the syringes 34 through tubing connected to a catheter, needle, or other fluid delivery connection (not shown) inserted into a patient at a vascular access site. According to various embodiments, the syringe 12 or 34 may be a pre-filled syringe, i.e., the syringe may be prefilled with a medical fluid, such as a contrast agent or saline, when provided by the syringe manufacturer. According to certain embodiments, the pre-filled syringe may be required to be spiked or otherwise punctured at the discharge end prior to an injection procedure to allow fluid to be expelled from the syringe into a fluid line to the patient, as described herein.

Figure 4:
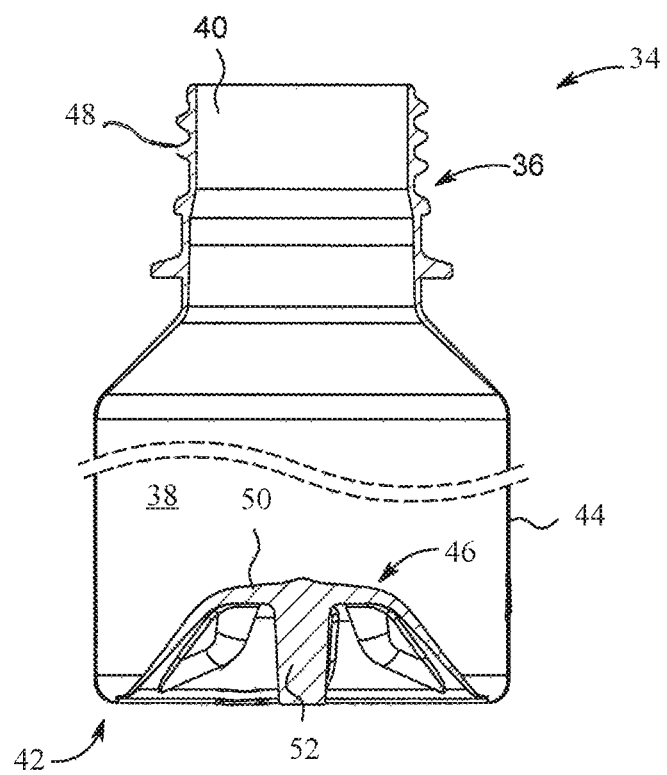
FIG. 4 is a side cross-sectional view of a syringe configured for use with the fluid delivery system of FIG. 3.

With reference to FIG. 4, the rolling diaphragm syringe 34 generally includes a hollow body 36 defining an interior volume 38. The body 36 has a forward or distal end 40, a rearward or proximal end 42, and a flexible sidewall 44 extending therebetween. The proximal end 42 may be configured to act as piston to pressurize the syringe interior to draw in or expel fluid therefrom, as described herein. The sidewall 44 of the rolling diaphragm syringe 34 defines a soft, pliable or flexible, yet self-supporting body that is configured to roll upon itself, as a "rolling diaphragm", under the action of the a drive member or piston of the fluid injector 10. The drive member/piston 19 may be configured to releasably engage a drive member engagement portion 52 at the proximal end 42 of the rolling diaphragm syringe 34 (examples of which are described in PCT/US2017/056747). In operation, the sidewall 44 is configured to roll such that its outer surface is folded and inverted in a radially inward direction as the drive member/piston 19 moves the proximal end 42 in a distal direction and unrolled and unfolded in the opposite manner in a radially outward direction as the drive member/piston 19 retract the proximal end 42 in a proximal direction.

With continued reference to FIG. 4, the rearward or proximal portion of the sidewall 44 connects to a closed end wall 46, and a forward or distal portion of the sidewall 44 defines a discharge neck 48 opposite the closed end wall 46. The closed end wall 46 may have a concave shape to facilitate the initiation of the inversion or rolling of the sidewall 44, enhance mechanical strength of the closed end wall 46, and/or to provide a receiving pocket to receive a distal end of drive member/piston 19. For example, the closed end wall 46 may define a receiving end pocket for interfacing directly with a similarly-shaped distal end of the drive member/piston 19. In some examples, at least a portion of the drive member/piston 19 may be shaped to substantially match the shape of the closed end wall 46 or, alternatively, pressure from the drive member/piston 19 as it is moved distally may conform the end wall 46 to substantially match the shape of at least a portion of the drive member/piston 19.

The end wall 46 may have a central portion 50 having a substantially dome-shaped structure and a drive member engagement portion 52 extending proximally from the central portion 50. The drive member engagement portion 52 is configured for releasably interacting with a corresponding engagement mechanism on the drive member/piston 19 of the fluid injector 10, for example as the drive member/piston is retracted. The rolling diaphragm syringe 34 may be made of any suitable medical-grade plastic or polymeric material, desirably a clear or substantially translucent plastic material. The material of the rolling diaphragm syringe 34 is desirably selected to meet the required tensile and planar stress requirements, water vapor transmission, and chemical/biological compatibility.

Figure 5:
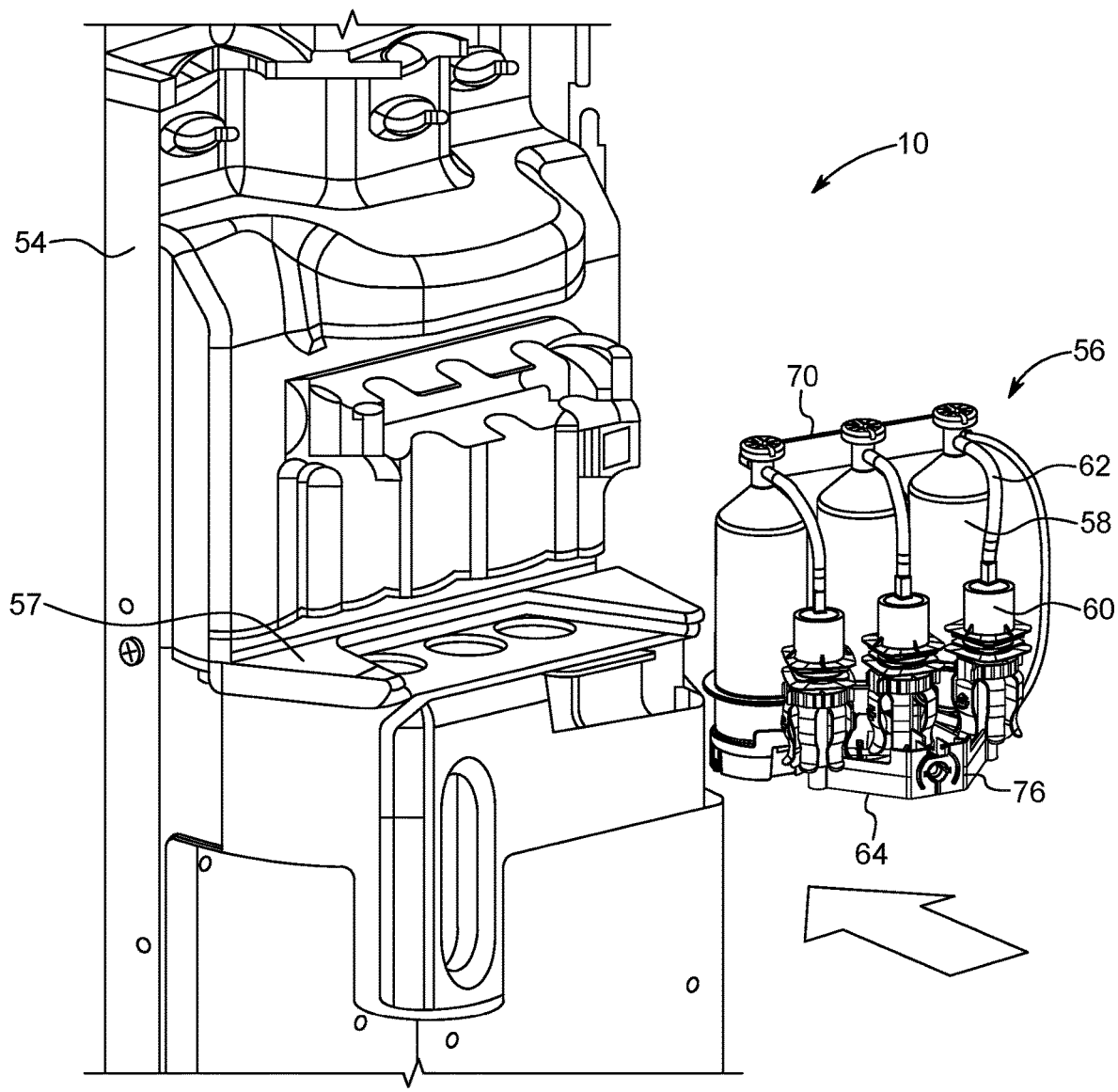
FIG. 5 is a perspective view of a fluid delivery system according to another example of the present disclosure.

With reference to FIG. 5, a fluid injector 10 is shown in accordance with another example of the present disclosure. The injector 10 has a housing 54 that encloses various mechanical drive components, electrical and power components necessary to drive the mechanical drive components, and control components, such as electronic memory and electronic control devices used to control operation of reciprocally movable pistons (not shown). The fluid injector 10 further has a multi-patient disposable system (MUDS) 56 that is removably connectable with the fluid injector 10. The MUDS 56 has one or more syringes or pumps 58. In some aspects, the number of syringes 58 corresponds to the number of pistons on the fluid injector 10. In some examples, such as shown in FIG. 6, the MUDS 56 has three syringes 58a-58c in a side-by-side arrangement. Each syringe 58a-58c has a bulk fluid connector 60 for connecting to a respective bulk fluid source (not shown) via a MUDS fluid path 62. The MUDS fluid path 62 may be formed as a flexible tube with a spike element at its terminal end that connects to the bulk fluid connector 60. Injector 10 and the corresponding MUDS 56 as illustrated in FIG. 5 are described in detail in WO 2016/112163, the disclosure of which is incorporated herein by this reference.

The MUDS 56 may comprise one or more syringes or pumps 58a-58c. In some aspects, the number of syringes 58 corresponds to the number of drive members/pistons on the fluid injector 10. In some examples, such as shown in FIGS. 5 and 6, the MUDS 56 has three syringes 58a-58c arranged in a side-by-side arrangement. Each syringe 58a-58c has a bulk fluid connector 60 for connecting to a respective bulk fluid source (not shown) via a MUDS fluid path 62. The MUDS fluid path 62 may be formed as a flexible tube that connects to the bulk fluid connector 60 having a spike element at its terminal end.

With reference to FIG. 6, the MUDS 56 has a frame 64 for supporting the one or more syringes 58a-58c. The syringes 58a-58c may be removably or non-removably connected to the frame 64. Each syringe 58a-58c has an elongated, substantially cylindrical syringe body. Each syringe 58a-58c has a filling port 66 in fluid communication with the MUDS fluid path 62 for filling the syringe 58a-58c with fluid from a bulk fluid source. Each syringe 58a-58c further has a discharge outlet or conduit 68 at the terminal portion of its distal end. The discharge outlet 68 of each syringe 58a-58c is in fluid communication with a manifold 70. A valve 72 is associated with each discharge outlet 68 and is operable between a filling position, where the filling port 66 is in fluid communication with the syringe interior while the discharge outlet 68 is in fluid isolation from the syringe interior, and a delivery position, where the discharge outlet 68 is in fluid communication with the syringe interior while the filling port 66 is in fluid isolation from the syringe interior. The manifold 70 has a fluid pathway that is in fluid communication with each syringe 58a-58c and with a fluid outlet line 74 in fluid communication with a port 76 configured for connecting to a single use fluid path element (not shown) for delivering fluid to the patient.

In various embodiments, for fluid injector 10, for example any of the fluid injectors shown in FIGS. 1, 3, and 5, the motor 31 (FIG. 2) provides the motive force to reciprocally drive the drive member/piston 19 in a distal direction and discharges fluid within the syringes 12, 34 or MUDS 56. The motor 31 may have drive components, such as gears and shafts, that are operatively connected to the drive member/piston 19 to reciprocally move the drive member/piston 19. Each motor 31 must be calibrated to correlate its operating characteristics, such as input current or output torque, to a flow rate or pressure and tolerances associated therewith. As described herein, calibration may be desirable to compensate for any variations or out of specification behavior from any of the different components of the fluid injectors 10, such as any variations in motor performance characteristics, particularly in fluid injectors with two or more syringes driven by two or more motors. For example, conversion of motor input torque for one motor 31 to an injector output pressure may be different for another motor 31. This variation may be further compounded by variations in tolerances of the drivetrain of the fluid injector 10. The accuracy of flow rate or pressure in a fluid injector 10 is directly correlative to a system and method used to calibrate the motor 31.

According to one example of the present disclosure, the fluid injector 10 discussed above with respect to FIGS. 1-6 may be configured to perform a multi-phase fluid injection which includes an injection of a first fluid F1 during a first phase, followed by an injection of a second fluid F2 during a second phase. During the first phase, the first fluid F1 is injected from at least a first syringe, for example the syringe 12a of FIG. 1 or one of the syringes 58b and/or 58c of FIGS. 5-6. During the second phase, the second fluid F2 is injected from at least a second syringe, for example the syringe 12b of FIG. 1 or syringe 58a of FIGS. 5-6. Hereinafter, the first and second syringes will be discussed with reference to FIGS. 5-6, and will thus be referred to as the first syringe 58b and the second syringe 58a. However, it is to be understood that the systems and methods described herein are equally applicable to any of the syringes 12a-12b of FIG. 1, an injector with two or more rolling diaphragm syringes 34 as illustrated in in FIGS. 3-4, or any other set of least two syringes in a fluid injection system.

The first fluid F1 of the first syringe 58b and the second fluid F2 of the second syringe 58a may be different fluids, such as medical fluids having different properties, such as different viscosities. Alternatively the first fluid F1 and the second fluid F2 may be the same fluid, for example medical fluid but at different concentrations or temperatures, or the same fluid being delivered at a different flow rate. For example, the first and second fluids F1, F2 may have one or more of a different viscosity, temperature, and/or density. In one example of the present disclosure, the first fluid F1 may be contrast media, as described herein, having a first viscosity and the second fluid F2 may be saline having a second viscosity which is typically lower than the first viscosity. In certain embodiments, the fluid injector may have a third syringe 58c, which may contain a third fluid F3 that may be the same or different that the first fluid F1 and second fluid F2. For example, F3 may be a contrast media, which may be the same as first fluid F1 or F3 may be a different contrast agent than F1, or F3 may be the same contrast type as F1 but at a different concentration than F1. During the first phase of the multi-phase injection, the first fluid F1, i.e. contrast, may be injected from the first syringe 58b at a first predetermined flow rate programmed into the injector 10. Delivery of the first fluid F1 at the first predetermined flow rate is achieved by applying a pressure to the first fluid F1 in the first syringe 58b, such as by driving the plunger of the first syringe 58b with the piston 19, where the necessary applied pressure to achieve the desired first predetermined flow rate is a function of the first viscosity of the first fluid F1. Because of the generally higher viscosity of the contrast of the first fluid F1, higher applied pressures are generally required to achieve a predetermined flow rate compared to the necessary applied pressure to achieve the same flow rate for a fluid with a lower viscosity, such as saline. Following the first phase of the multi-phase injection, the second phase includes injection of the second fluid F2, i.e. saline, from the second syringe 58a. The second predetermined flow rate of the second fluid F2 may be the same as, greater than, or lower than the first predetermined flow rate of the first fluid F1. In fluid injections where the first and second predetermined flow rates are targeted to be the same, due to the differences between the first viscosity of the first fluid F1 and the second viscosity of the second fluid F2, the pressure required to deliver the second fluid F2 may differ from the pressure required to deliver the first fluid F1. In the present example, the pressure applied to the first fluid F1, i.e. contrast media, is generally higher than the pressure applied to the second fluid F2, i.e. saline, in order to obtain the same flow rate. In other examples, the second predetermined flow rate of the second fluid F2 may be different than the first predetermined flow rate of the first fluid F1, yet the pressures necessary to achieve the predetermined flow rates of the first fluid F1 and the second fluid F2 may still be different.

FIGS. 8A-8D are graphs depicting percentage of desired volume delivered as a function of pressure in an exemplary injections system having a single container, wherein the fluid injector has active control, and wherein impedance correction is not applied. It is to be understood, however, that this disclosure may relate to fluid injectors having multiple fluid containers.

With further reference to FIGS. 8A-8D, a volume of medical fluid intended to be injected into a patient may have an accepted range of uncertainty, or specification limit (i.e., a range of volume delivered values that are acceptable, as indicated by dashed lines in each of FIGS. 8A-8D). Each of FIGS. 8A-8D shows an upper specification limit percentage and a lower specification limit percentage for acceptable tolerance. As shown in FIGS. 8A-8D, embodiments of the injection system with active control but without impedance and/or capacitance correction often inject volumes of fluid that are below the lower specification limit for a given injection protocol. This error becomes more pronounced as pressure increases (pressure shown on x-axis), and/or as the volume of fluid delivered from the syringe decreases. Data points are connected in the graphs and fitted to curves. It is to be understood that the volume inaccuracy discussed herein—i.e., the under-delivery of fluid due to impendence and/or capacitance characteristics of the fluid injector and/or fluid—is a condition generally associated with "closed" systems or systems with active control, such as those discussed with respect to FIGS. 5 and 6. Thus, the correction discussed herein, an example of which is discussed in connection to FIGS. 9 and 10A-10D, is particularly applicable to such injector systems. Other injectors, such as those shown in FIGS. 1-4, may also utilize the methods described herein, for example when a stopcock, pinch valve, and/or high pressure crack valve are incorporated into the injection system, such as in the tubing set. Additionally, in a system without active control, if it is not desired that the volume due to capacitance leak out or be injected into a patient, the methods described herein may be applied to over-drive the compliance volume and immediately pull back the equivalent compliance volume position of the piston at the end of an injection phase, after the reservoir is fluidly isolated from the fluid path.

Figure 9:
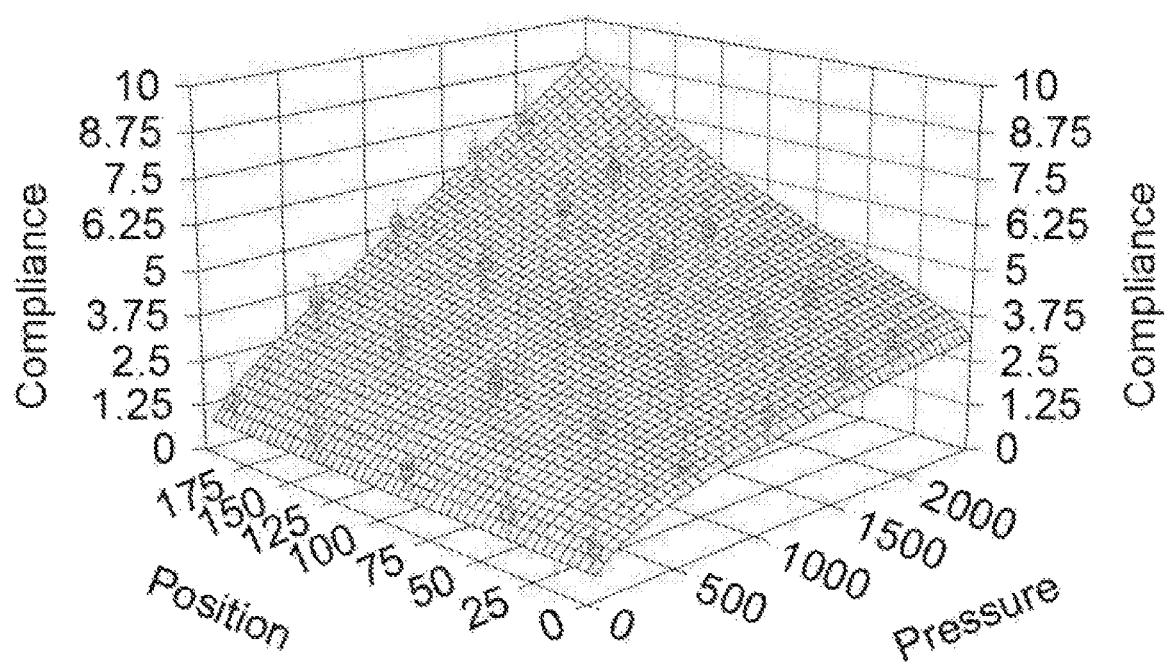
FIG. 9 is a graph showing undelivered volume of fluid associated with compliance in an injection system according to the present disclosure as a function of remaining injection volume and pressure.
Figure 10A:
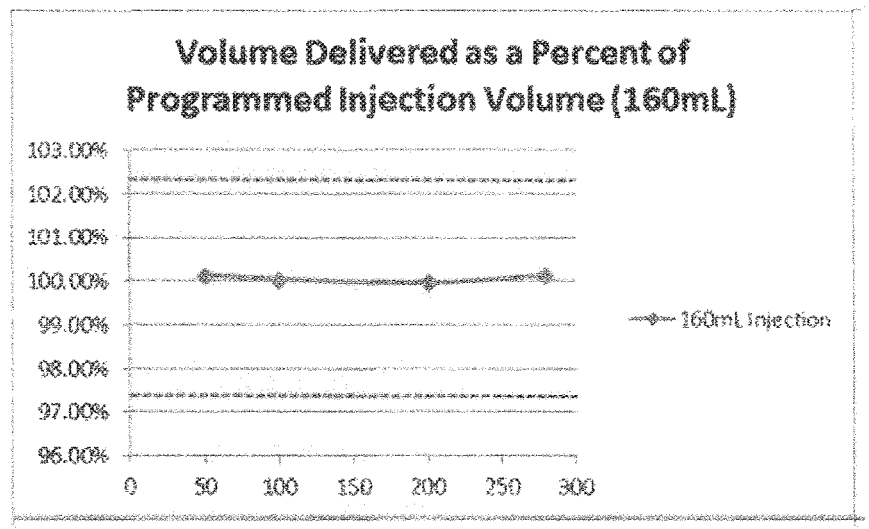
FIG. 10A is a graph showing percentage of desired fluid delivered from a 160 milliliter (mL) volume as a function of pressure for an exemplary single-container injector system having active control and applying a correction according to the present disclosure.
Figure 10B:
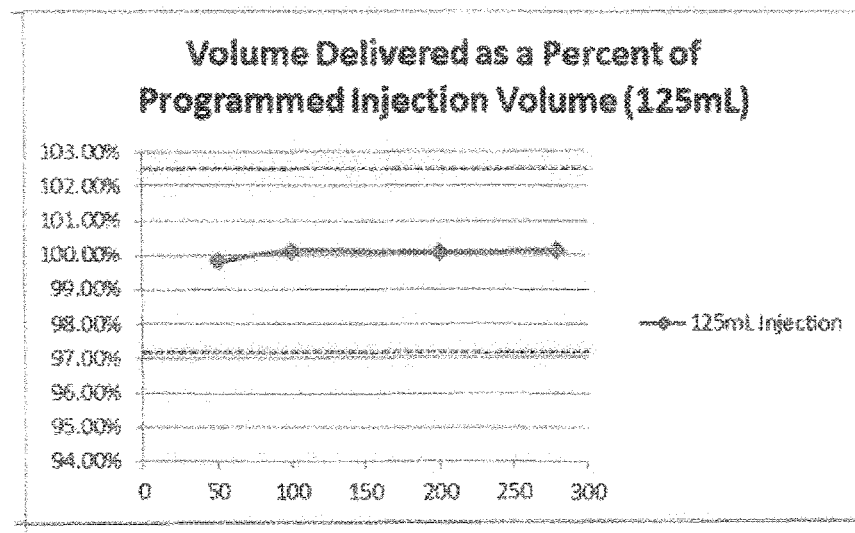
FIG. 10B is a graph showing percentage of desired fluid delivered from a 125 milliliter (mL) volume as a function of pressure for an exemplary single-container injector system having active control and applying a correction according to the present disclosure.
Figure 10C:
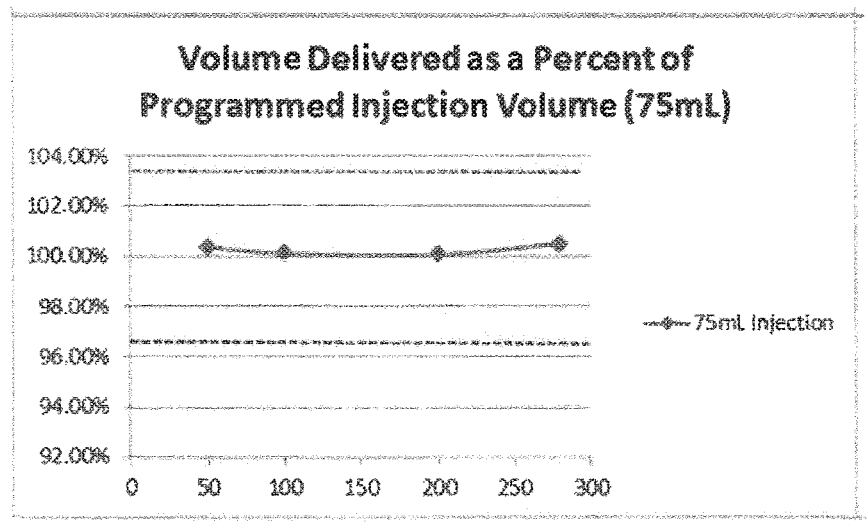
FIG. 10C is a graph showing percentage of desired fluid delivered from a 75 milliliter (mL) volume as a function of pressure for an exemplary single-container injector system having active control and applying a correction according to the present disclosure.
Figure 10D:
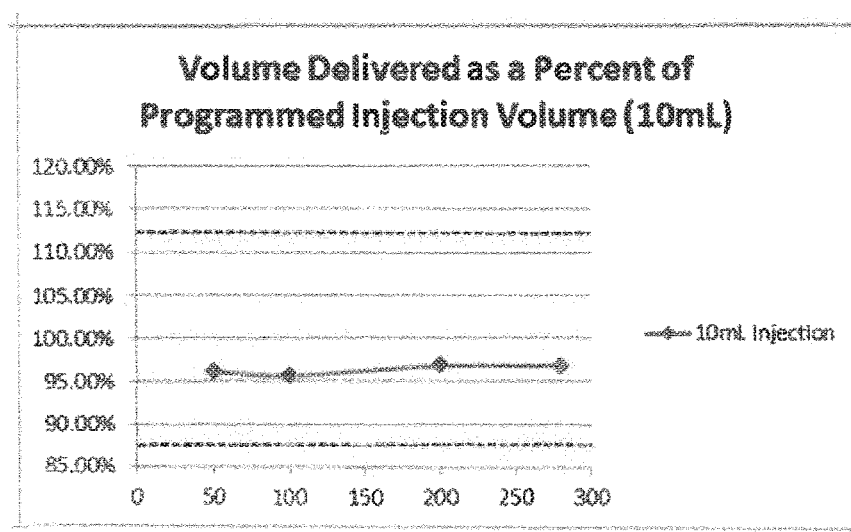
FIG. 10D is a graph showing percentage of desired fluid delivered from a 10 milliliter (mL) volume as a function of pressure for an exemplary single-container injector system having active control and applying a correction according to the present disclosure.

FIG. 9 shows a three-dimensional graph showing a volume of undelivered fluid as a function of pressure and injection volume remaining in a container, such as a syringe. As shown for embodiments illustrated in FIG. 9, the data points determined for under-delivery of fluid at a set pressure and set remaining volume in the container are plotted on a three-dimensional graph, and a surface is mapped according to these data. By mapping the under-delivered volume of the system and fitting to a 3D surface, an equation can be derived which can predict volume inaccuracy based on reservoir volume and pressure. It should be noted that other systems may result in other 3D surface curves for under-delivered volume as a factor of injection volume remaining and pressure, and alternative surface equations may be determined to establish the correlation between the three variables, so that accurate fluid delivery protocols for accounting for impedance and/or capacitance properties of the system may be developed.

With further reference to FIG. 9, the impedance and capacitance properties of an exemplary fluid injector result in an under-delivery according to the following Equation (3):

$$z^{-1} = c \cdot y^{0.5} + b/x^{0.5} + a \tag{3}$$

wherein z is the system volume compliance (C), such as over- or under-delivered volume (which may be measured in any appropriate volume unit such as in milliliters ("mL")); y the available volume in the at least one fluid reservoir at the time of injection ($V_1$), x is the pressure of the fluid with the at least one fluid reservoir ($P_1$) (which may be measured in any appropriate pressure unit, such as in pounds per square inch ("psi") or kilopascals (kPA)), c is the position scalar (A), b is the pressure constant (B), and a is the compensation factor (O), which may be constants for the particular surface. When the under-delivered volume of fluid is determined thusly, the fluid to be injected into a patient may be corrected for and increased by the appropriate amount to compensate for the volume lost due to capacitance and impedance of the fluid injector and/or fluid. The fluid injector can over-drive the piston by the distance calculated to deliver the predicted volume that is under-delivered (i.e., z) to ensure an accurate injection dose of the fluid to the patient. The value "z" may also be referred to as a "correction volume."

The values of the coefficients for Equation (3) may have values that are appropriate to fit the surface curve for the observed injection parameters. In certain embodiment, constant c may have a value ranging from −0.01 to −0.025, b may have a value ranging from 8.00 to 12.00, and a may have a value ranging from 0.050 to 0.150, such that the calculated compliance values may range from greater than 0 mL to 20 mL, for example from 3 mL to 10 mL. In other embodiments, a may have a value ranging from 0.112 to 0.115, b may have a value ranging from 10.35 to 10.45, and c may have a value ranging from −0.01465 to −0.01495, such that the calculated compliance values may range from greater than 0 mL to 20 mL, for example from 3 mL to 10 mL. For example, with further reference to FIG. 9, coefficients according to one embodiment may have values c=−0.014863432, b=10.39086, and a=0.11422056 are determined as best fitting the surface curve illustrated in FIG. 9. It is to be understood, however that the values of coefficients a, b, and c depend on the impedance and/or capacitance characteristics for a particular injector system, syringe configuration, or medical fluid properties, such as injector component slack (for example in motor components, and interfaces between injector components), capacitance swelling of the syringes, capacitance swelling of the tubing set, fluid characteristics (such as temperature, concentration and/or viscosity), etcetera. Thus, examples of three-dimensional surfaces as in FIG. 9 may vary by fluid injector, disposable syringes and fluid path sets used in the fluid injector, and injected fluid.

With reference to FIGS. 5 and 9, the determination of a correction volume according to Equation (1) may be performed at any time, for example at the beginning of each day or prior to the first use of a multi-use syringe set (such as a MUDS as described in relation to FIG. 5) for each fluid injector used, or performed on each syringe prior to, or during, each injection procedure, or could be a factory default setting stored once and used for every injection throughout the life of that system. The method according to the present disclosure may be stored on memory on the computing device 300, and applied automatically by the controller of the computing device, for example when a new multi-use syringe set is installed, and/or with user input.

Applying Equation (1) as in FIG. 9 to the exemplary multi-use syringe set for a fluid injector, exemplary steps for practicing an example consistent with above disclosure are as follows. Ensure there is sufficient volume in the syringe for the injection protocol, i.e., the amount of fluid to be injected into a patient for a protocol plus extra volume of fluid to compensate for under delivered volume due to impedance and/or capacitance within the system. This can conservatively be accomplished by adding a sufficient excess of fluid, such as 5 to 10 mL excess in one non-limiting example for a 200 mL syringe in a CT contrast/saline injection protocol, or approximately 7 mL (or other volume of fluid, such as 11 mL) to the programmed volume of fluid to be loaded into the syringe according to the example of Equation (1) with the coefficients and parameters described above. This will ensure that the syringe contains sufficient fluid to compensate for under-delivery by allowing over-drive of the piston to deliver the calculated under-delivered volume to the patient after the injector delivers the non-corrected volume. In certain embodiments, it may also be necessary to load even further fluid into the syringe to compensate for fluid volume used in a priming/purging operation, so that after prime/purge, sufficient excess fluid remains over the non-corrected volume to allow for under-delivery compensation. In a situation where the syringe does not contain a sufficient volume including non-corrected volume and under-delivery compensation volume, the injector may alert the technician that there is insufficient volume to deliver the correct amount of fluid. An example of this may be to warn the user of insufficient volume if they program a 100 mL injection and there is less than 107 mL in the syringe after purging. For injections of 200 mL, the injector would fill the syringe up to 215 mL volume and purge forward to 207 mL to have sufficient excess fluid available to compensate for under-delivery. Alternatively, it is known that the under-delivered volume is minimized when only small volumes of fluid are to be injected using larger volume syringes. Thus, when the piston is near the distal end of the syringe, only about 3 mL of excess volume needs to be accessible to compensate for under-delivery. In certain examples, this may be further reduced by setting the zero position to be at the recoil zero as described herein, and driving the piston past that zero to the maximum pressure allowed. The processor may be programmed to account for various scenarios when applying the methods of the present disclosure to minimize fluid waste and account for accurate delivery of fluid to the patient.

FIGS. 10A-10D are graphs depicting percentage of desired volume delivered as a function of pressure in an exemplary injection system discussed with respect to FIGS. 8A-8D and 9, wherein the fluid injector has active control, and wherein a correction volume according to the present disclosure has been calculated and applied by the injector processor according to methods described herein. As may be seen in FIGS. 10A-10D, the percentage of desired volume is more consistent as a function of pressure, and falls within the Specification Limit indicating delivery of accurate volumes of fluid as required by the injection protocol. By correcting for the volume inaccuracy components of the system, the accuracy of the volume delivered should consistently fall within Specification Limits.

Figure 11:
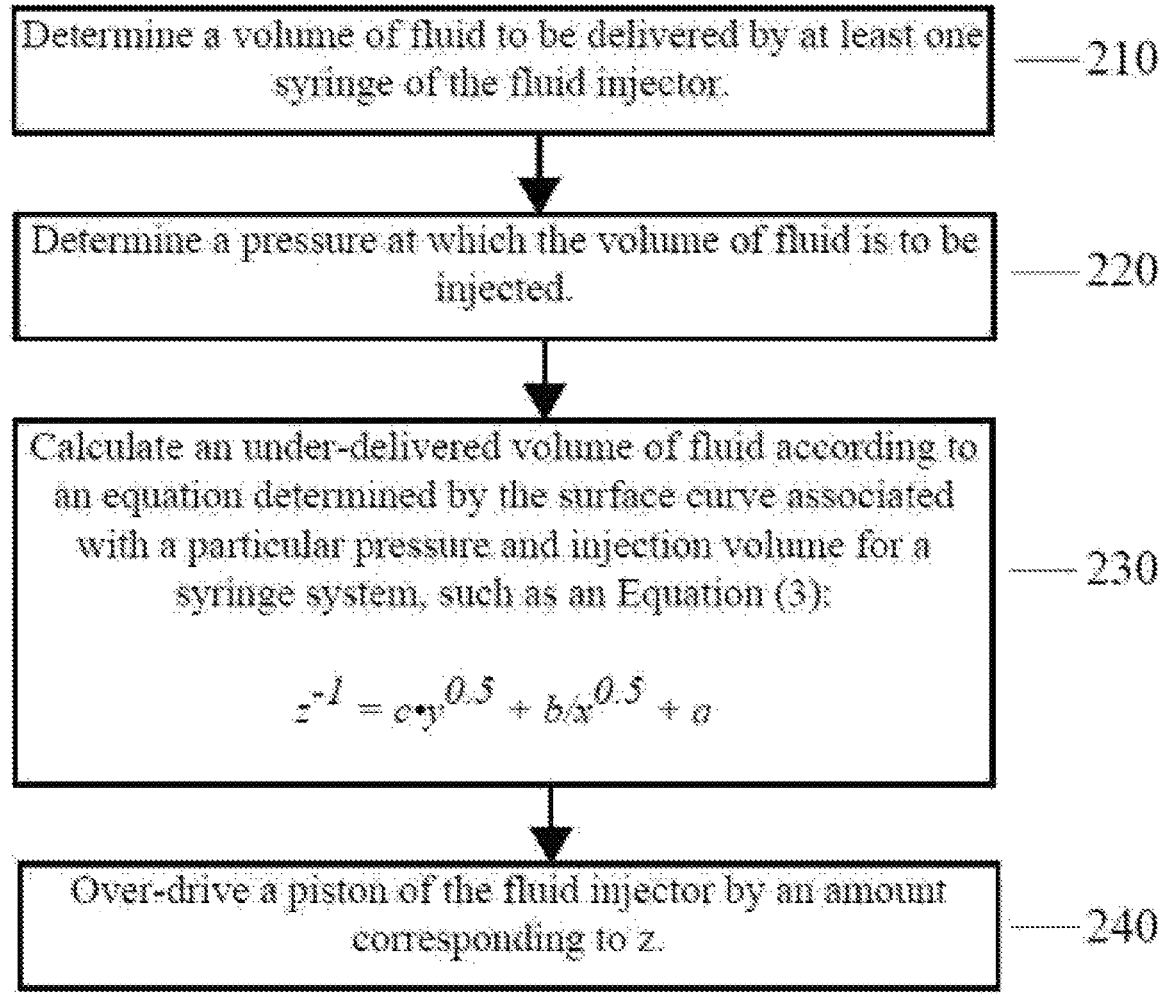
FIG. 11 is a flow chart providing steps of a method according to the present disclosure.

FIG. 11 includes a flow chart illustrating steps of an exemplary method for correcting a fluid volume of fluid for an injection protocol according to certain embodiments of the present disclosure. Step 210 comprises determining a volume of a fluid to be delivered by at least one syringe of the fluid injector. Step 220 comprises determining a pressure at which the volume of fluid is to be injected. Step 230 comprises calculating an under-delivered volume of fluid according to an equation determined by the surface curve associated with a particular pressure and injection volume for a syringe system, such as Equation (3):

$$z^{-1} = c \cdot y^{0.5} + b/x^{0.5} + a \quad (3)$$

wherein z is the system volume compliance (C), such as over- or under-delivered volume (which may be measured in any appropriate volume unit such as in milliliters ("mL")); y the available volume in the at least one fluid reservoir at the time of injection ($V_1$), x is the pressure of the fluid with the at least one fluid reservoir ($P_1$) (which may be measured in any appropriate pressure unit, such as in pounds per square inch ("psi")), c is the position scalar (A), b is the pressure constant (B), and a is the compensation factor (O), which may be constants for the particular surface based on or determined by the impedance characteristics of the fluid injector. Step 240 comprises over-driving a piston of the fluid injector by an amount corresponding to z to deliver an accurate amount of fluid to a patient.

Figure 12:
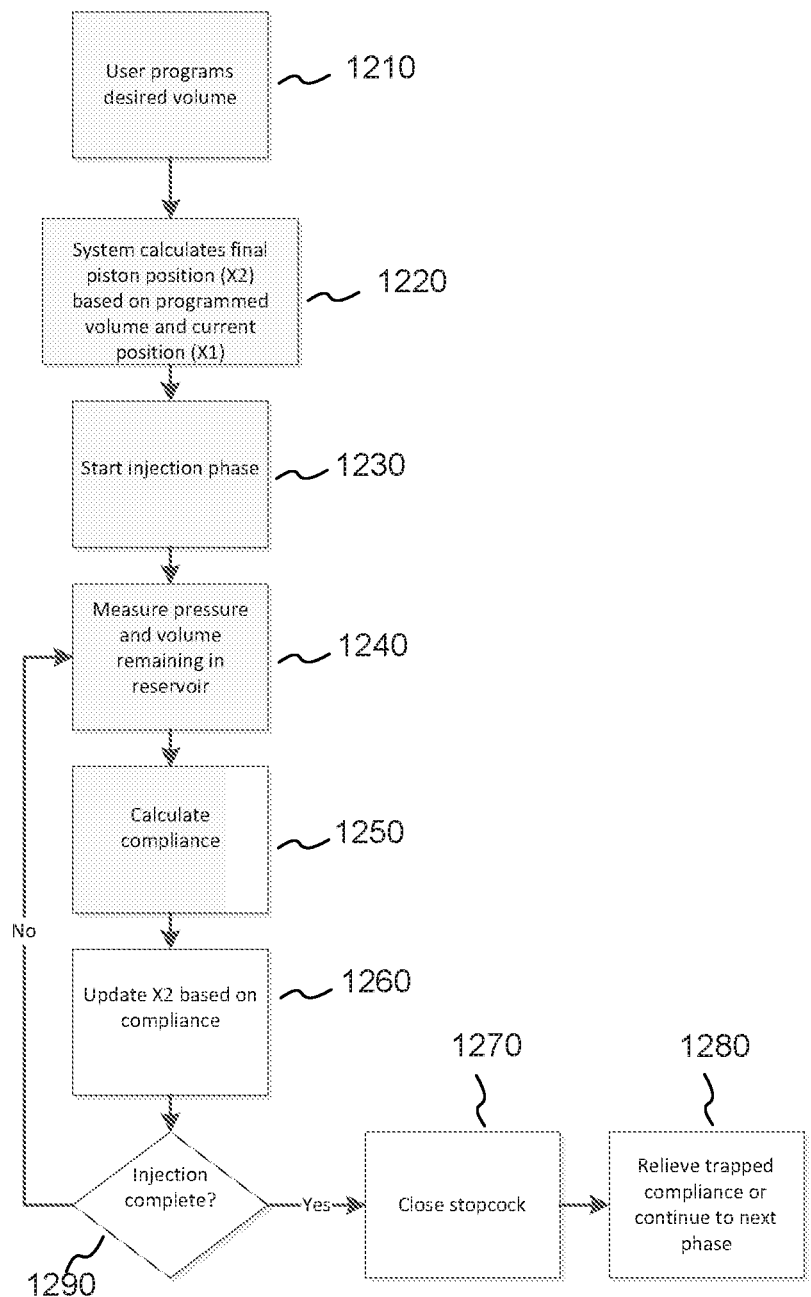
FIG. 12 is a flow chart providing steps of a method of volume compensation during an injection protocol according to one embodiment.

FIG. 12 is a flow chart illustrating steps of an exemplary method for correcting a fluid volume of fluid for an injection protocol according to certain embodiments of the present disclosure. The user programs the desired volume(s) of the fluid(s) to be delivered from a fluid reservoir 1210, such as a syringe, during an injection procedure. The processor of the fluid injection system then calculates the initial final drive member position, such as a piston, (X2) 1220 based on the programmed or current volume of the fluid reservoir and the current position of the drive member (X1), and the fluid injector begins the fluid injection procedure 1230. The system then measures the pressure of the fluid and the volume of fluid remaining in the reservoir 1240, either real-time during the injection or the piston reaches the initial final drive member position (X2). Based on the system characteristics and the pressure and volume measurements, the system calculates the compliance of the system 1250 and then updates the final drive member position from the initial final drive member position X2 to a compliance corrected final drive member position X2' 1260. Based on the compliance corrected position X2', the system then determines whether the injection is complete 1290, i.e., is the drive member at the final compliance corrected position X2'. If the system determines that the drive member is not at the final compliance corrected position X2', then the system may move back and repeat steps 1240, 1250, 1260, and 1290, repeatedly if necessary, until the system determines that the injection is complete and the drive member is at the final compliance corrected position X2'. If the system determines that the drive member is at the final compliance corrected position X2', then the system closes the valve (e.g., a stopcock) 1270. Closing the stopcock in step 1270 traps the compliance of the fluid in the reservoir as stored compliance. The system may optionally relieve the stored or trapped compliance or, alternatively continue to the next phase of a multiphase injection protocol 1280. If the later occurs, when the fluid from the reservoir will contain the stored compliance and the next injection phase that utilizes that reservoir will account for the compliance in the calculation of the fluid volume (i.e., the system may not have to adjust the distance that the drive member moves at the final drive member position X2, since the compliance has already been accounted for by the stored compliance.

EXAMPLE 1

To determine the compliance of the system empirically, the following test setup was used. A multi-use disposable system (MUDS) 56 according to FIG. 6 was inserted into the injector system 10 shown in FIG. 5 with a pressure transducer attached to each reservoir to capture real time pressure data. Each reservoir was filled to a set volume. An outlet fluid line was connected to port 76 was then attached to the MUDS 56 with a stopcock valve 72 closed. The system was then pressurized to a predetermined pressure by advancing the piston of the specified reservoir 58a-58c. Once the desired pressure was reached, the piston was stopped. The stopcock 72 was then opened and the displaced lab water was measured on an analytical balance. Using density and mass, the volume of this displaced fluid was calculated. This displaced fluid volume was recorded as the compliance volume for that specific combination of plunger position and pressure. Data points were obtained at fill volumes from 200 mL to 10 mL, and pressures achieved at each of those positions ranging from 25 psi to 300 psi. This data then was used to create a surface map shown in FIG. 9 of the compliance of that reservoir in the system. Multiple MUDS sets 56 were used along with all three reservoir positions and multiple injector systems to generate a robust characterization of system compliance for injector 10. This surface plot represents an equation fit to the data, where the equation has inputs of plunger position and pressure, with an output of compliance volume. Two feedback loops, piston position and pressure, were included in this calculation of compliance, meaning that the system was able to use this relationship to calculate compliance at any point within the expected use conditions.

The following is an illustrative example of the method according to the present disclosure with reference to FIG. 9. Step A is initiating an injection of 100 mL at 5 mL/s which initially has a 20 second duration. Step B is to measure the pressure of the injection which reaches a steady state of 200 psi. Step C is to apply Equation (3) to the above parameters in Steps A and B, which predicts non-corrected volume delivered to be 4.05 mL less than the programmed volume. Step D is to adjust the final position of the injection to occur after delivery of 104.05 mL of fluid to the patent, for example by setting the final position at 104.05 mL less than the volume position at the start of the injection. (If the starting fill position is 107 mL, then the final position of the injector after completion of the procedure should be 2.95 mL). Step E is to deliver the corrected-for volume of fluid to the patient and close the stopcock after the final position is reached, isolating the fluid in the reservoir. Step E relieves the pressure generated by the trapped compliance of 4.05 mL to return the syringe to 0 psi and its nominal volume state. In certain embodiment, relieving the trapped compliance pressure may not be necessary when conducting a subsequent phase injection and may be taken into account in the compliance value for the subsequent phase.

Although the disclosure has been described in detail for the purpose of illustration based on what is currently considered to be the most practical and preferred examples, it is to be understood that such detail is solely for that purpose and that the disclosure is not limited to the disclosed examples, but, on the contrary, is intended to cover modifications and equivalent arrangements. For example, it is to be understood that the present disclosure contemplates that, to the extent possible, one or more features of any example can be combined with one or more features of any other example.

The invention claimed is:

1. A method for correcting a volume of fluid delivered by a fluid injector system during an injection procedure using one or more fluid reservoirs, the method comprising:

determining a fluid volume of a first fluid in at least one of the fluid reservoirs of the fluid injector system;

determining a pressure at which a first programmed volume of the first fluid is to be injected;

determining a system volume compliance according to Equation (1) for the at least one fluid reservoir, one or more fluid injector mechanical components associated with the at least one fluid reservoir, and one or more tubing system components:

$$C_1 = A_1 \cdot V_1 + B_1 \cdot P_1 + O_1 \quad (1)$$

where $C_1$ is the system volume compliance of the at least one fluid reservoir, $A_1$ is a position scalar of the at least one fluid reservoir, $V_1$ is available volume of the at least one fluid reservoir, $B_1$ is a pressure constant of the at least one fluid reservoir, $P_1$ is a pressure of fluid within the at least one fluid reservoir, and $O_1$ is a compensation factor of the at least one fluid reservoir;

predicting a volume compliance factor of fluid in the at least one fluid reservoir according to Equation (2):

$$VC_1 = PV_1 + C_1 \quad (2)$$

where $VC_1$ is the volume compliance factor of the fluid in the at least one fluid reservoir, $PV_1$ is a programmed volume of the first fluid, and $C_1$ is the system volume compliance of the at least one fluid reservoir; and compensating for the volume compliance factor to deliver a programmed fluid volume by one of over-driving a distance that a drive member travels in the at least one fluid reservoir, under-driving the distance that the drive member travels in the at least one fluid reservoir, increasing a delivery time of the fluid in the at least one fluid reservoir, and decreasing the delivery time of the fluid in the at least one fluid reservoir.

2. The method of claim 1, wherein the at least one fluid reservoir comprises at least one first fluid reservoir containing the first fluid and at least one second fluid reservoir containing a second fluid, wherein the method further comprises:

determining a fluid volume of the second fluid in the at least one second fluid reservoir of the fluid injector system;

determining a second pressure at which a programmed volume of the second fluid is to be injected;

determining a system volume compliance according to Equation (1) for the at least one second fluid reservoir, one or more fluid injector mechanical components associated with the second reservoir, and one or more tubing system components:

$$C_2 = A_2 \cdot V_2 + B_2 \cdot P_2 + O_2 \quad (1)$$

where $C_2$ is the system volume compliance for the at least one second fluid reservoir, $A_2$ is a position scalar for the at least one second fluid reservoir, $V_2$ is available volume for the at least one second fluid reservoir, $B_2$ is a pressure constant for the at least one second fluid reservoir, $P_2$ is a pressure of fluid within the at least one second fluid reservoir, and $O_2$ is a compensation factor for the at least one second fluid reservoir;

predicting a volume compliance factor of the fluid in the at least one second reservoir according to Equation (2):

$$VC_2 = PV_2 + C_2 \quad (2)$$

where $VC_2$ is the volume compliance factor of the at least one second fluid reservoir, $PV_2$ is a programmed volume of the at least one second fluid reservoir, and $C_2$ is a system volume compliance of the at least one second fluid reservoir; and compensating for the volume compliance factor of the at least one second fluid reservoir to deliver the programmed fluid volume of the second fluid by one of over-driving a distance that a drive member travels in the at least one second fluid reservoir, under-driving a distance that the drive member travels in the at least one second fluid reservoir, increasing a delivery time of the second fluid in the at least one second fluid reservoir, and decreasing the delivery time of the second fluid in the at least one second fluid reservoir.

3. The method of claim 1, wherein the at least one fluid reservoir comprises at least one first fluid reservoir containing the first fluid, at least one second fluid reservoir containing a second fluid, and at least one third fluid reservoir containing a third fluid.

4. The method of claim 1, further comprising determining whether the at least one fluid reservoir contains at least a volume of fluid corresponding to the programmed volume plus an amount of fluid equal to the system volume compliance according to Equation (1).

5. The method of claim 3, wherein the at least one first fluid reservoir, the at least one second fluid reservoir, and the at least one third fluid reservoir are independently selected from a group consisting of a syringe, a rolling diaphragm syringe, a peristaltic pump, and a compressible bag.

6. The method of claim 3, wherein at least one of the at least one first fluid reservoir, the at least one second fluid reservoir, and the at least one third fluid reservoir is a syringe.

7. The method of claim 6, wherein the syringe comprises a plunger operatively connected to the drive member, wherein the drive member is selected from a linear actuated piston and a motor driven piston.

8. The method of claim 3, wherein at least one of the at least one first fluid reservoir, the at least one second fluid reservoir, and the at least one third fluid reservoir is a rolling diaphragm syringe.

9. The method of claim 6, wherein the system volume compliance of Equation (1) is determined according to Equation (3):

$$z^{-1} = c \cdot y^{0.5} + b/x^{0.5} + a \quad (3)$$

where z is the system volume compliance (C), c is the position scalar (A), y is the available volume in the at least one fluid reservoir ($V_1$), b is the pressure constant (B), x is the pressure of the fluid with the at least one fluid reservoir ($P_1$), and a is the compensation factor (O).

10. The method of claim 9, wherein a has a value ranging from 0.112 to 0.115, b has a value ranging from 10.35 to 10.45, and c has a value ranging from −0.01465 to −0.01495.

11. The method of claim 1, wherein compensating for the volume compliance factor of the at least one fluid reservoir comprises:

over-driving the distance that the drive member travels in the at least one fluid reservoir; and injecting an additional volume of the first fluid equal to the volume compliance factor.

12. The method of claim 11, further comprising closing a valve to fluidly isolate the at least one fluid reservoir from a patient after injecting the additional volume of the first fluid.

13. The method of claim 1, wherein compensating for the volume compliance factor of the at least one fluid reservoir comprises increasing a delivery time of the first fluid in the at least one fluid reservoir.

14. The method of claim 13, wherein increasing the delivery time of the first fluid comprises increasing the delivery time by an amount sufficient to deliver an additional volume of the first fluid equal to the volume compliance factor.

15. The method of claim 1, further comprising reporting to a user a value corresponding to a corrected volume of a fluid being delivered to a patient from the at least one fluid reservoir, wherein the corrected volume accounts for the programmed volume and the system volume compliance.

16. A fluid delivery system comprising:

a fluid injector;

at least one first fluid reservoir configured to contain a first fluid;

at least one first drive member configured to drive the first fluid from the at least one first fluid reservoir; and a controller in operable communication with the at least one first drive member, wherein the controller comprises computer readable memory containing instructions that, when executed by the controller, causes the controller to:

determine a fluid volume of the first fluid in the at least one first fluid reservoir of the fluid injector system;

determine a pressure at which a first programmed volume of the first fluid is to be injected;

determine a system volume compliance according to Equation (1) for the at least one first fluid reservoir, one or more fluid injector mechanical components associated with the at least one first fluid reservoir, and one or more tubing system components:

$$C_1 = A_1 \cdot V_1 + B_1 \cdot P_1 + O_1 \tag{1}$$

where $C_1$ is the system volume compliance of the at least one first fluid reservoir, $A_1$ is a position scalar of the at least one first fluid reservoir, $V_1$ is available volume of the at least one first fluid reservoir, $B_1$ is a pressure constant of the at least one first fluid reservoir, $P_1$ is a pressure of the first fluid within the at least one first fluid reservoir, and $O_1$ is a compensation factor of the at least one first fluid reservoir;

predict a volume compliance factor of the first fluid in the at least one first fluid reservoir according to Equation (2):

$$VC_1 = PV_1 + C_1 \tag{2}$$

where $VC_1$ is the volume compliance factor of the first fluid in the at least one first fluid reservoir, $PV_1$ is a programmed volume of the first fluid, and $C_1$ is the system volume compliance of the at least one first fluid reservoir; and compensate for the volume compliance factor to deliver a programmed fluid volume by one of over-driving a distance that the at least one first drive member travels in the at least one first fluid reservoir, under-driving a distance that the at least one first drive member travels in the at least one first fluid reservoir, increasing a delivery time of the first fluid in the at least one first fluid reservoir, and decreasing the delivery time of the first fluid in the at least one first fluid reservoir.

17. The fluid delivery system according to claim 16, wherein the controller is configured to determine the system volume compliance of Equation (1) according to Equation (3):

$$z^{-1} = c \cdot y^{0.5} + b/x^{0.5} + a \tag{3}$$

where z is the system volume compliance (C), c is the position scalar (A), y is the available volume in the at least one first fluid reservoir ($V_1$), b is the pressure constant (B), x is the pressure of the first fluid with the at least one first fluid reservoir ($P_1$), and a is the compensation factor (O).

18. The fluid delivery system of claim 17, wherein a has a value ranging from 0.112 to 0.115, b has a value ranging from 10.35 to 10.45, and c has a value ranging from −0.01465 to −0.01495.

19. The fluid delivery system of claim 16, wherein the computer readable memory containing instructions that, when executed by the controller, causes the controller to compensate for the volume compliance factor; causes the controller to:

over-drive the distance that the drive member travels in the at least one first fluid reservoir; and inject an additional volume of the first fluid equal to the volume compliance factor.

20. The fluid delivery system of claim 16, wherein the computer readable memory containing instructions that, when executed by the controller, causes the controller to compensate for the volume compliance factor; causes the controller to:

increase the delivery time of the first fluid in the at least one first fluid reservoir by an amount sufficient to deliver an additional volume of the first fluid equal to the volume compliance factor.

\* \* \* \* \*

UNITED STATES PATENT AND TRADEMARK OFFICE
CERTIFICATE OF CORRECTION

PATENT NO. : 11,478,581 B2
APPLICATION NO. : 16/621164
DATED : October 25, 2022
INVENTOR(S) : McDermott et al.

It is certified that error appears in the above-identified patent and that said Letters Patent is hereby corrected as shown below:

In the Specification
In Column 1, Line 45, delete "over-rate" and insert -- to over-rate --, therefor.
In Column 3, Line 52, delete "expelling" and insert -- expelling of --, therefor.
In Column 5, Line 2, delete "volume" and insert -- volume of --, therefor.
In Column 5, Line 4, delete "compliance" and insert -- compliance of --, therefor.
In Column 5, Line 55, delete "(V1)" and insert -- (V1), --, therefor.
In Column 5, Line 66, delete "addition" and insert -- additional --, therefor.
In Column 7, Line 1, delete "(V1)" and insert -- (V1), --, therefor.
In Column 7, Line 15, delete "addition" and insert -- additional --, therefor.
In Column 9, Line 48, delete "how" and insert -- of how --, therefor.
In Column 10, Line 37, delete "ompliance" and insert -- compliance --, therefor.
In Column 11, Line 42, delete "results" and insert -- result --, therefor.
In Column 12, Line 63, delete "form" and insert -- from --, therefor.
In Column 13, Line 30, delete "volume" and insert -- volume of --, therefor.
In Column 13, Line 32, delete "compliance" and insert -- compliance of --, therefor.
In Column 14, Line 52, delete "in draw" and insert -- to draw --, therefor.
In Column 14, Line 55, delete "determine" and insert -- determined --, therefor.
In Column 15, Line 28, delete "staring" and insert -- starting --, therefor.
In Column 15, Line 60, delete "According" and insert -- According to --, therefor.
In Column 16, Line 51, delete "volume" and insert -- volume of --, therefor.
In Column 16, Line 58, delete "volume" and insert -- volume of --, therefor.
In Column 18, Line 48, delete "the a" and insert -- the --, therefor.
In Column 20, Line 56, delete "in in" and insert -- in --, therefor.
In Column 21, Line 6, delete "that" and insert -- than --, therefor.
In Column 22, Line 46, delete "y the" and insert -- y is the --, therefor.
In Column 24, Line 48, delete "y the" and insert -- y is the --, therefor.
In Column 25, Line 28, delete "later" and insert -- latter --, therefor.

Signed and Sealed this
Sixth Day of June, 2023

Katherine Kelly Vidal
*Director of the United States Patent and Trademark Office*